(12) United States Patent
Moriwaki et al.

(10) Patent No.: US 10,519,182 B2
(45) Date of Patent: Dec. 31, 2019

(54) METHOD FOR PRODUCING FLAVONOID INCLUSION COMPOUND

(71) Applicants: Masamitsu Moriwaki, Suzuka (JP); Kentaro Kumoi, Suzuka (JP); Makoto Ozeki, Yokohama (JP)

(72) Inventors: Masamitsu Moriwaki, Suzuka (JP); Kentaro Kumoi, Suzuka (JP); Makoto Ozeki, Yokohama (JP)

(73) Assignee: TAIYO KAGAKU CO., LTD., Yokkaichi-Shi (JP)

( * ) Notice: Subject to any disclaimer, the term of this patent is extended or adjusted under 35 U.S.C. 154(b) by 0 days.

(21) Appl. No.: 16/097,120

(22) PCT Filed: Jan. 31, 2018

(86) PCT No.: PCT/JP2018/003177
§ 371 (c)(1),
(2) Date: Oct. 26, 2018

(87) PCT Pub. No.: WO2019/021510
PCT Pub. Date: Jan. 31, 2019

(65) Prior Publication Data
US 2019/0248825 A1 Aug. 15, 2019

(30) Foreign Application Priority Data

Jul. 28, 2017 (JP) .................................. 2017-147121

(51) Int. Cl.
| | | |
|---|---|---|
| C07H 17/07 | (2006.01) |
| A23L 3/3499 | (2006.01) |
| A61K 47/40 | (2006.01) |
| A61K 8/60 | (2006.01) |
| A61K 8/73 | (2006.01) |
| A61K 31/7048 | (2006.01) |
| A23F 3/16 | (2006.01) |
| A23L 2/02 | (2006.01) |
| A23L 2/44 | (2006.01) |
| A23L 21/10 | (2016.01) |
| A23F 5/24 | (2006.01) |

(52) U.S. Cl.
CPC ............ *C07H 17/07* (2013.01); *A23L 3/3499* (2013.01); *A61K 8/602* (2013.01); *A61K 8/738* (2013.01); *A61K 31/7048* (2013.01); *A61K 47/40* (2013.01); *A23F 3/16* (2013.01); *A23F 5/24* (2013.01); *A23L 2/02* (2013.01); *A23L 2/44* (2013.01); *A23L 21/10* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 2006/0153936 | A1 | 7/2006 | Tsuzaki |
| 2008/0187622 | A1 | 8/2008 | Moriwaki et al. |
| 2009/0143317 | A1 | 6/2009 | Ono et al. |
| 2012/0083460 | A1 | 4/2012 | Emura et al. |
| 2015/0272184 | A1 | 10/2015 | John et al. |

FOREIGN PATENT DOCUMENTS

| | | | |
|---|---|---|---|
| JP | H05-310776 | A | 11/1993 |
| JP | H07-10898 | A | 1/1995 |
| JP | H07-107972 | A | 4/1995 |
| JP | 3135912 | B2 | 2/2001 |
| JP | 2003-261593 | A | 9/2003 |
| JP | 3833775 | B2 | 10/2006 |
| JP | 2008-271839 | A | 11/2008 |
| JP | 4202439 | B2 | 12/2008 |
| JP | 2011-225586 | A | 11/2011 |
| JP | 4902151 | B2 | 3/2012 |
| JP | 5000864 | B2 | 8/2012 |
| JP | 2013-215155 | A | 10/2013 |
| JP | 2015-188450 | A | 11/2015 |
| WO | WO 2005/030975 | A1 | 4/2005 |
| WO | WO 2006/070883 | A1 | 7/2006 |
| WO | WO 2010/110328 | A1 | 9/2010 |

OTHER PUBLICATIONS

US 5,885,989 A, 03/1999, Miyake et al. (withdrawn)
JP5000884B2, published 2012, machine translation.*
Japan Patent Office communication for Japanese Patent Application No. 2018-526605, dated Aug. 3, 2018.
Feglines et al., "Bioavailability of the flavanone naringenin and its glycosides in rats", Am J Physiol: Gastrointest Liver Physiol, 279: G1148-G1154, 2000.
Habauzit et al., "Increased bioavailability of hesperetin-7-glucoside compared with hesperidin results in more efficient prevention of bone loss in adult ovariectomised rats", British Journal of Nutrition, vol. 102, pp. 976-984, 2009.

(Continued)

Primary Examiner — Layla D Berry
(74) Attorney, Agent, or Firm — Birch, Stewart, Kolasch & Birch, LLP

(57) ABSTRACT

A method for producing a flavonoid inclusion compound, including a cleaving step including treating a sparingly soluble flavonoid having a rhamnoside structure with an enzyme having a rhamnosidase activity in the presence of a cyclodextrin to cleave a rhamnose. According to the production method of the present invention, a flavonoid inclusion compound and a composition of flavonoid glycosides having excellent solubility in water can be efficiently produced, so that the compound and composition can be suitably utilized in the fields of medicaments, foodstuff, health foods, foods for specified health use, cosmetics, and the like.

7 Claims, 2 Drawing Sheets

(56) References Cited

OTHER PUBLICATIONS

Makino et al., "Anti-allergic effects of enzymatically modified isoquercitrin (α-oligoglucosyl quercetin 3-O-glucoside), quercetin 3-O-glucoside, α-oligoglucosyl rutin, and quercetin, when administered orally to mice," Journal of Natural Medicines, vol. 67, pp. 881-886, Oct. 2013.

Makino et al., "Enzymatically Modified Isoquercitrin, α-Oligoglucosyl Quercetin 3-O-Glucoside, Is Absorbed More Easily than Other Quercetin Glycosides or Aglycone after Oral Administration in Rats", Biol. Pharm. Bull, vol. 32, No. 12, pp. 2034-2040, 2009.

Shulman et al., "Enhancement of Naringenin Bioavailability by Complexation with Hydroxypropoyl-β-Cyclodextrin", PLoS ONE, vol. 6, Issue 4, Apr. 2011, e18033, pp. 1-8.

Çelik et al., "Antioxidant Capacity of Quercetin and its Glycosides in the Presence of β-cyclodextrins: Influence of Glycosylation on Inclusion Complexation," J Incl Phenom Macrocycl Chem, vol. 83, 2015 (Published online Oct. 1, 2015), pp. 309-319, XP035913950.

Extended European Search Report, dated Jun. 17, 2019, for European Application No. 18799420.7.

Gullón et al., "Rutin: A Review on Extraction, Identification and Purification Methods, Biological Activities and Approaches to Enhance its Bioavailability," Trends in Food Science & Technology, vol. 67, 2017 (Available online Jul. 11, 2017), pp. 220-235, XP002791716.

Kohara et al., "Enzymatically Modified Isoquercitrin Supplementation Intensifies Plantaris Muscle Fiber Hypertrophy in Functionally Overloaded Mice," Journal of International Society of Sports Nutrition, vol. 14, 2017 (Published online Sep. 2, 2017), pp. 1-7, XP002791719.

Lee et al., "Glucosylation of Flavonol and Flavanones by Bacillus Cyclodextrin Glucosyltransferase to Enhance their Solubility and Stability," Food Chemistry, vol. 229, 2017 (Available online Feb. 16, 2017), pp. 75-83, XP002791691.

Motoyama et al., "Atheroprotective and Plaque-stabilizing Effects of Enzyrnatically Modified Isoquercitrin in Atherogenic apoE-deficient Mice," Nutrition, vol. 25, 2009, pp. 421-427, XP025992593.

Pérez-Abril et al., "Systematic Investigation and Molecular Modelling of Complexation between Several Groups of Flavonoids and HP-β-cyclodextrins," Journal of Functional Foods, vol. 36, 2017 (Available online Jul. 5, 2017), pp. 122-131, XP085154605.

Shimoda et al., "Glycosylation of Quercetin with Cultured Plant Cells and Cyclodextrin Glucanotransferase," Natural Product Communications, vol. 9, No. 5, 2014, pp. 647-648, XP002791718.

Wang et al., "An Effective Biphase System Accelerates Hesperidinase-catalyzed Conversion of Rutin to Isoquercitrin," Scientific Reports, vol. 5, Published Mar. 3, 2015, pp. 1-8, XP002791699.

Xiao et al., "Advances in the Biotechnological Glycosylation of Valuable Flavonoids," Biotechnology Advances, vol. 32, 2014 (Available online Apr. 26, 2014), pp. 1145-1156, XP002791717.

Yang et al., "Host-guest System of Hesperetin and β-cyclodextrin or its Derivatives: Preparation, Characterization, Inclusion Mode, Solubilization and Stability," Materials Science and Engineering C, vol. 59, 2016 (Available online Oct. 23, 2015), pp. 1016-1024, XP029329708.

* cited by examiner

FIG. 1 HPLC Chromatogram of Example 39
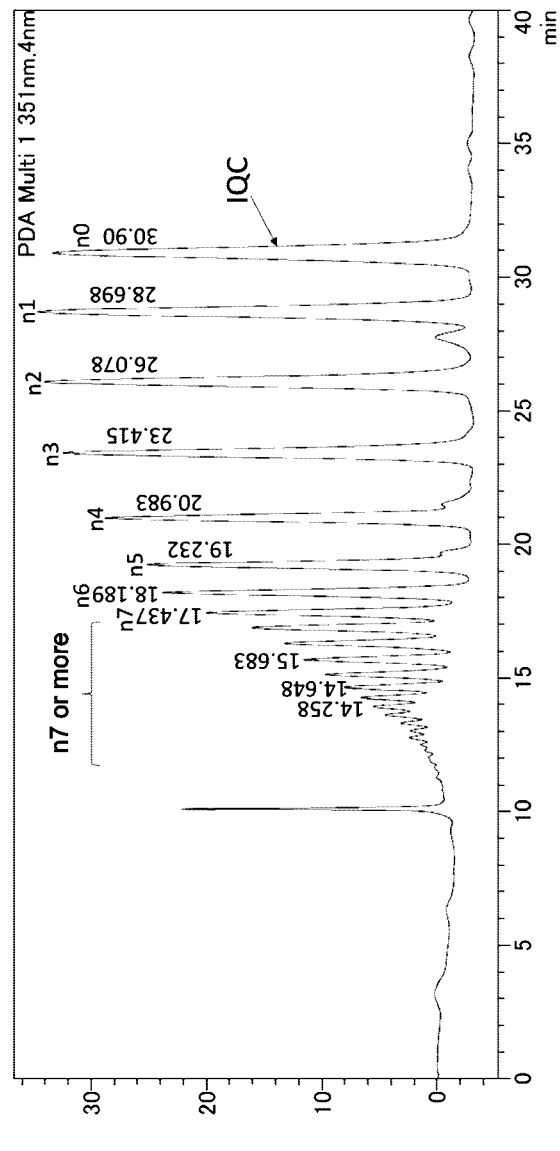
n0 to n7 is a value of n in the general formula (1), and n0 is IQC.

FIG. 2  HPLC Chromatogram of Example 40
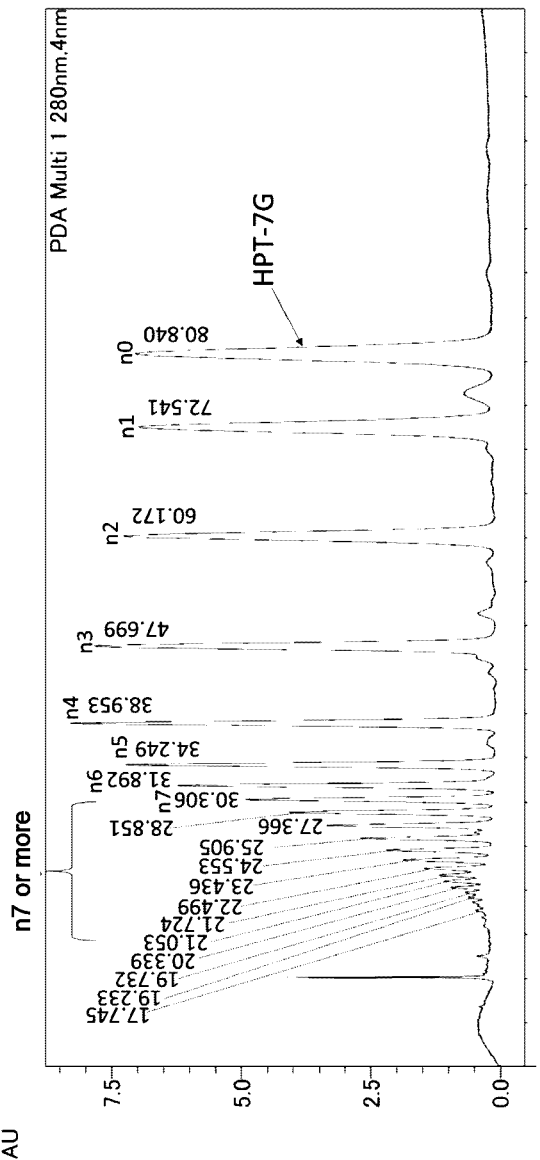

METHOD FOR PRODUCING FLAVONOID INCLUSION COMPOUND

TECHNICAL FIELD

The present invention relates to a method for producing a flavonoid inclusion compound, a method for producing a composition of flavonoid glycosides, a flavonoid inclusion compound, a flavonoid inclusion compound-containing composition, a composition of isoquercitrin glycosides, a composition of glycosides of hesperetin-7-glucoside, a composition of glycosides of naringenin-7-glucoside, foodstuff, a medicament or cosmetics containing these compounds or compositions, and a method for improving a solubility of a sparingly soluble flavonoid having a rhamnoside structure.

BACKGROUND ART

Since flavonoids have an anti-oxidation effect, the flavonoids have been used in prevention of deterioration for flavor of foods, prevention of fading of color and the like, and lists of foods additives, already existing additives and antioxidants of Japan have reported numerous substances containing flavonoids as an active ingredient such as catechins, enzymatically modified rutins, rutin extracts, tea extracts, Chinese bayberry extracts. In addition, as physiological actions of flavonoids, anti-tumor, lowering of cholesterols, lowering of blood pressure, lowering of blood sugars, reduction in body fats and the like have been reported, and flavonoids have been widely used in medicaments, foodstuff, health foods, foods for specified health use, cosmetics, and the like.

Flavonoids are contained in vegetables, fruits, teas and the like, and 3,000 or more kinds of flavonoids have been known, but many of flavonoids are sparingly soluble in water, so that it is difficult to use flavonoids for foods, beverages, medicaments or cosmetics that would require readily water-soluble ability, as in refreshing beverages, aqueous agents and the like. For example, a solubility of hesperidin or rutin which is a representative flavonoid is 0.01% or less, so that it is difficult to use it for refreshing beverages, cosmetic lotions or the like.

Sparingly soluble flavonoids can be classified to ones having a rhamnoside structure and ones without a rhamnoside structure, and it has been reported that isoquercitrin, hesperetin-7-glucoside, naringenin, or naringenin-7-glucoside in which rhamnose is cleaved has higher bioavailability in rats than rutin, hesperidin, or naringin having a rhamnoside structure (Non-Patent Publications 1 to 3).

In addition, it has been known that bioavailability is improved and physiological effects are effectively shown by including a sparingly soluble flavonoid with a cyclodextrin or subjecting a sparingly soluble flavonoid to glycosidation. As to an inclusion compound, for example, it has been reported that an isoquercitrin (1 M)-γ-cyclodextrin (5 M) inclusion compound has a higher body absorption rate than isoquercitrin (Patent Publication 1), that in an experimentation with mice, a hesperetin-β-cyclodextrin inclusion compound or the like has higher bioavailability (AUC: 0 to 9 hours), and higher effects of allergic reaction-suppressing actions, bloodstream-improving actions, and sensitivity to cold-improving actions than hesperetin (Patent Publication 2), and that a naringenin-hydroxypropyl β-cyclodextrin inclusion compound has an elevated bioavailability (rat), a reduced VLDL (very low lipoprotein), and an increased rate of glucose clearance as compared to naringenin (Non-Patent Publication 4). As to glycosidation, for example, it has been reported that anti-allergic effects by mice are in the order of "enzymatically modified rutin<isoquercitrin<enzymatically modified isoquercitrin," and an enzymatically modified isoquercitrin in which a rhamnose is removed and which is water-soluble shows highest effects (Non-Patent Publication 5).

In addition to the above publications, a method for cleaving a rhamnose from a sparingly soluble flavonoid having a rhamnoside structure has been disclosed in, for example, Patent Publications 3 to 6. A method for including a sparingly soluble flavonoid with a cyclodextrin has been disclosed in, for example, Patent Publications 2, 7 and 8. A method for subjecting a sparingly soluble flavonoid to glycosidation has been disclosed in, for example, Patent Publications 9 and 10. Additionally, Patent Publication 11 discloses a method for solubilization including allowing a sparingly soluble flavonoid to be copresent with a soybean saponin and/or a composition of glycosides of malonyl isoflavone as a method for making a sparingly soluble flavonoid readily water-soluble.

In addition, a method for improving water solubility characterized by combining a sparingly soluble flavonoid with readily water-soluble flavonoid glycosides as a method for improving a solubility of a sparingly soluble flavonoid (Patent Publications 3 to 4 and 12), and a water-soluble flavonoid characterized in that the flavonoid contains a sparingly soluble flavonoid-β-cyclodextrin and a glycosyl hesperidin (Patent Publication 8) have been disclosed.

PRIOR ART REFERENCES

Patent Publications

Patent Publication 1: Japanese Patent No. 5002072
Patent Publication 2: Japanese Patent No. 5000884
Patent Publication 3: Japanese Patent No. 4902151
Patent Publication 4: Japanese Patent No. 3833775
Patent Publication 5: Japanese Patent No. 4498277
Patent Publication 6: Japanese Patent No. 5985229
Patent Publication 7: Japanese Patent No. 3135912
Patent Publication 8: Japanese Patent No. 5000373
Patent Publication 9: Japanese Patent No. 4202439
Patent Publication 10: Japanese Patent No. 3989561
Patent Publication 11: Japanese Patent Laid-Open No. 2011-225586
Patent Publication 12: Japanese Patent Laid-Open No. Hei-07-10898

Non-Patent Publications

Non-Patent Publication 1: *British Journal of Nutrition*, 102, 976-984, 2009
Non-Patent Publication 2: *Biological & Pharmaceutical Bulletin*, 32(12), 2034-2040, 2009
Non-Patent Publication 3: *American Journal of Physiology*: Gastrointestinal and Liver Physiology, 279, 1148-1154, 2000
Non-Patent Publication 4: PLOS ONE (4), e18033, 2011
Non-Patent Publication 5: *Journal of natural Medicines*, October, 67(4), 881-6, 2013

SUMMARY OF THE INVENTION

Problems to be Solved by the Invention

However, it is not said that the production methods disclosed in the above prior arts publications are excellent in production efficiencies, and the obtained flavonoids do not sufficiently satisfy a solubility in water, so that further improvements are desired.

An object of the present inventions is to newly provide an easy and efficient method for producing a flavonoid inclusion compound and a composition of flavonoid glycosides having an excellent solubility in water. Also, an object is to provide a flavonoid inclusion compound having an excellent solubility in water, a flavonoid inclusion compound-containing composition, a composition of isoquercitrin glycosides, a composition of glycosides of hesperetin-7-glucoside, a composition of glycosides of naringenin-7-glucoside, foodstuff, medicaments or cosmetics containing these compounds or compositions, and a method for improving a solubility of a sparingly soluble flavonoid having a rhamnoside structure.

Means to Solve the Problems

The present invention relates to:

[1] A method for producing a flavonoid inclusion compound, including a cleaving step including treating a sparingly soluble flavonoid having a rhamnoside structure with an enzyme having a rhamnosidase activity in the presence of a cyclodextrin to cleave a rhamnose;

[2] a method for producing a composition of flavonoid glycosides, including a glycosidation step including treating a flavonoid inclusion compound obtained according to a method as defined in the above [1] with a glycosyltransferase to subject the flavonoid inclusion compound to glycosidation;

[3] a method for producing a composition of flavonoid glycosides, including a cleaving step including treating a sparingly soluble flavonoid having a rhamnoside structure with an enzyme having a rhamnosidase activity in the presence of a cyclodextrin to cleave a rhamnose, and a glycosidation step including treating a flavonoid inclusion compound obtained through the cleaving step with a glycosyltransferase to subject the flavonoid inclusion compound to glycosidation;

[4] a flavonoid inclusion compound containing isoquercitrin included by γ-cyclodextrin, wherein a molar ratio of the isoquercitrin and the γ-cyclodextrin (γ-cyclodextrin/isoquercitrin) is from 0.9 to 1.8, and wherein a solubility of the isoquercitrin in water is 2% or more;

[5] a flavonoid inclusion compound containing isoquercitrin included by γ-cyclodextrin, wherein a molar ratio of the isoquercitrin and the γ-cyclodextrin (γ-cyclodextrin/isoquercitrin) is from 0.9 to 4.0, and wherein a solubility of the isoquercitrin in water is 2.5% or more;

[6] a flavonoid inclusion compound containing isoquercitrin included by β-cyclodextrin, wherein a molar ratio of the isoquercitrin and the β-cyclodextrin (β-cyclodextrin/isoquercitrin) is from 1.0 to 3.0, and wherein a solubility of the isoquercitrin in water is 0.1% or more;

[7] a flavonoid inclusion compound containing hesperetin-7-glucoside included by a cyclodextrin, wherein a molar ratio of the hesperetin-7-glucoside and the cyclodextrin (cyclodextrin/hesperetin-7-glucoside) is from 1.0 to 3.0, and wherein a solubility of the hesperetin-7-glucoside in water is 0.01% or more;

[8] a flavonoid inclusion compound containing naringenin-7-glucoside included by β-cyclodextrin, wherein a molar ratio of the naringenin-7-glucoside and the β-cyclodextrin (β-cyclodextrin/naringenin-7-glucoside) is from 1.0 to 3.0, and wherein a solubility of the naringenin-7-glucoside in water is 0.01% or more;

[9] a flavonoid inclusion compound-containing composition containing a flavonoid inclusion compound as defined in any one of the above [4] to [8] and a rhamnose, wherein a molar ratio of the flavonoid inclusion compound and the rhamnose (rhamnose/flavonoid) is from 0.8 to 1.2;

[10] a flavonoid inclusion compound-containing composition containing a flavonoid inclusion compound as defined in any one of the above [4] to [8] and a sparingly soluble flavonoid having a rhamnoside structure, wherein a molar ratio of a flavonoid in the flavonoid inclusion compound and the sparingly soluble flavonoid (sparingly soluble flavonoid/flavonoid in the inclusion compound) is from 0.001 to 0.1;

[11] a composition of isoquercitrin glycosides containing a compound represented by the following general formula (1):

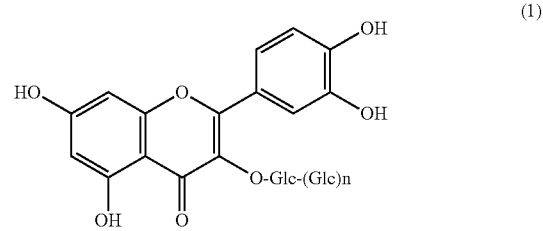

where in the general formula (1), Glc means a glucose residue, and n means an integer of 0 or 1 or more, and wherein the content of glycosides having n=0 is 10% by mol or more and 30% by mol or less, the content of glycosides having n=1 to 3 is 50% by mol or less, and the content of glycosides having n=4 or more is 30% by mol or more, of the composition of glycosides;

[12] a composition of glycosides of hesperetin-7-glucoside containing a compound represented by the following general formula (2):

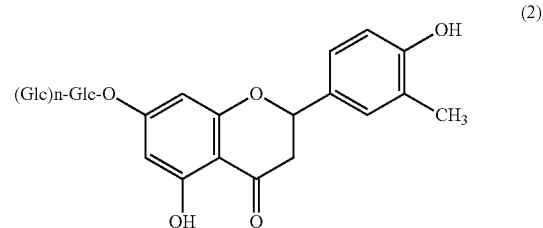

where in the general formula (2), Glc means a glucose residue, and n means an integer of 0 or 1 or more, and wherein the content of glycosides having n=0 is 10% by mol or more and 30% by mol or less, the content of glycosides having n=1 to 3 is 50% by mol or less, and the content of glycosides having n=4 or more is 30% by mol or more, of the composition of glycosides;

[13] a composition of glycosides of naringenin-7-glucoside containing a compound represented by the following general formula (3):

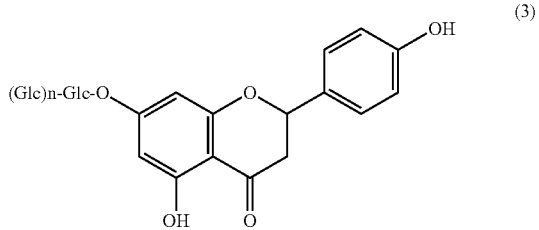

where in the general formula (3), Glc means a glucose residue, and n means an integer of 0 or 1 or more, and wherein the content of glycosides having n=0 is 10% by mol or more and 30% by mol or less, the content of glycosides having n=1 to 3 is 50% by mol or less, and the content of glycosides having n=4 or more is 30% by mol or more, of the composition of glycosides;

[14] foodstuff containing one or more compounds or compositions selected from the group consisting of a flavonoid inclusion compound obtained according to a method as defined in the above [1], a composition of flavonoid glycosides obtained according to a method as defined in the above [2] or [3], a flavonoid inclusion compound as defined in any one of the above [4] to [8], a flavonoid inclusion compound-containing composition as defined in the above [9] or [10], a composition of isoquercitrin glycosides as defined in the above [11], a composition of glycosides of hesperetin-7-glucoside as defined in the above [12], and a composition of glycosides of naringenin-7-glucoside as defined in the above [13];

[15] a medicament containing one or more compounds or compositions selected from the group consisting of a flavonoid inclusion compound obtained according to a method as defined in the above [1], a composition of flavonoid glycosides obtained according to a method as defined in the above [2] or [3], a flavonoid inclusion compound as defined in any one of the above [4] to [8], a flavonoid inclusion compound-containing composition as defined in the above [9] or [10], a composition of isoquercitrin glycosides as defined in the above [11], a composition of glycosides of hesperetin-7-glucoside as defined in the above [12], and a composition of glycosides of naringenin-7-glucoside as defined in the above [13];

[16] cosmetics containing one or more compounds or compositions selected from the group consisting of a flavonoid inclusion compound obtained according to a method as defined in the above [1], a composition of flavonoid glycosides obtained according to a method as defined in the above [2] or [3], a flavonoid inclusion compound as defined in any one of the above [4] to [8], a flavonoid inclusion compound-containing composition as defined in the above [9] or [10], a composition of isoquercitrin glycosides as defined in the above [11], a composition of glycosides of hesperetin-7-glucoside as defined in the above [12], and a composition of glycosides of naringenin-7-glucoside as defined in the above [13]; and

[17] a method for improving a solubility of a sparingly soluble flavonoid having a rhamnoside structure, including mixing the sparingly soluble flavonoid having a rhamnoside structure with a flavonoid inclusion compound obtained according to a method as defined in the above [1] or a flavonoid inclusion compound as defined in any one of the above [4] to [8] in a medium such that a molar ratio of a flavonoid in the flavonoid inclusion compound to the sparingly soluble flavonoid (flavonoid in the inclusion compound/sparingly soluble flavonoid) is from 0.1 to 0.9.

Effects of the Invention

According to the present inventions, an easy and efficient method for producing a flavonoid inclusion compound and a composition of flavonoid glycosides having an excellent solubility in water is newly provided. In addition, a flavonoid inclusion compound having an excellent solubility in water, a flavonoid inclusion compound-containing composition, a composition of isoquercitrin glycosides, a composition of glycosides of hesperetin-7-glucoside, a composition of glycosides of naringenin-7-glucoside, foodstuff, medicaments or cosmetics containing these compounds or compositions, and a method for improving a solubility of a sparingly soluble flavonoid having a rhamnoside structure can be provided.

BRIEF DESCRIPTION OF THE DRAWINGS

FIG. 1 shows an HPLC chromatogram of Example 39.
FIG. 2 shows an HPLC chromatogram of Example 40.

MODES FOR CARRYING OUT THE INVENTION

As a result of studying the above objects, the present inventors have found that a flavonoid inclusion compound can be produced at the same time as the cleavage of a rhamnose from a sparingly soluble flavonoid having a rhamnoside structure in the presence of a cyclodextrin to thereby cleave the rhamnose, so that a flavonoid inclusion compound can be more efficiently produced than the conventional method in which the cleaving step and the inclusion step have been separately carried out. Further surprisingly, the inventors have found that the flavonoid inclusion compound obtained according to the production method has more excellent solubility in water than a flavonoid inclusion compound produced according to the convention method. In the present invention, in addition to the cyclodextrin, various cyclic oligosaccharides can be used in the same manner. A cyclic oligosaccharide as used herein shows a compound in which monosaccharides are linked in a cyclic form, and more specifically, examples include cyclodextrin, cyclodextran, cyclofructan, cycloalternan, cluster dextrin, and the like. In the following description, an embodiment using cyclodextrin will be explained as an example; however, the present invention is not intended to be limited thereto, and other cyclic oligosaccharides can be used in the same manner.

The method for producing a flavonoid inclusion compound of the present invention includes a cleaving step including treating a sparingly soluble flavonoid having a rhamnoside structure with an enzyme having a rhamnosidase activity in the presence of a cyclodextrin to cleave a rhamnose.

The cleaving step is a step of cleaving a rhamnose from a sparingly soluble flavonoid having a rhamnoside structure to obtain an inclusion compound of a flavonoid without a rhamnoside structure and a cyclodextrin (also referred to as "flavonoid inclusion compound"). The cleaving step can be carried out while allowing to stand in a medium such as water or while stirring, or the air in a headspace of a reaction system may be replaced with an inert gas such as nitrogen to prevent oxidation or browning during the reaction, and also an antioxidant such as ascorbic acid can be added to a reaction system. The cleaving step can be terminated by a known method such as a method including a method of deactivating enzymes by heating or the like.

The sparingly soluble flavonoid having a rhamnoside structure includes ones selected from flavonols, flavanones, flavones, and isoflavones, and ones having a structure in which one or more, preferably two or more hydroxyl groups are bonded to a benzene ring of a flavonoid backbone and which holds a rhamnose can be used. Here, "sparingly soluble" refers to a solubility in water at 25° C. of 1.0% by mass or less, preferably 0.1% or less, and more preferably 0.01% by mass or less. Specific examples include rutin, hesperidin, narirutin, naringin, diosmin, eriocitrin, myricitrin, neohesperidin, luteolin-7-rutinoside, delphinidin-3-rutinoside, cyanidin-3-rutinoside, isorhamnetin-3-rutinoside, kaempferol-3-rutinoside, apigenin-7-rutinoside, acacetin-7-rutinoside, derivatives thereof and the like. The derivatives include acetylated compounds, malonylated compounds, methylated compounds and the like.

The amount of the sparingly soluble flavonoid having a rhamnoside structure used is not particularly limited, and the amount used can be preferably from 0.1 to 20% by mass, more preferably from 1 to 15% by mass, and even more preferably from 2 to 14% by mass in the reaction system. When the sparingly soluble flavonoids having a rhamnoside structure are used in two or more kinds, the amount used refers to a total amount thereof.

Raw materials containing a sparingly soluble flavonoid having a rhamnoside structure used in the production method of the present invention are not particularly needed to be purified, but the raw materials are preferably purified. The content of the sparingly soluble flavonoid having a rhamnoside structure in the above raw materials is not particularly limited, and the sparingly soluble flavonoid having a content of preferably 5% or more, more preferably 20% or more, even more preferably 50% or more, even more preferably 80% or more and even more preferably 90% or more can be used.

The cyclodextrin (CD) which is present in the cleaving step is not particularly limited, and more preferably one or more members selected from the group consisting of β-cyclodextrin (β-CD), branched β-cyclodextrin (branched β-CD), and γ-cyclodextrin (γ-CD) can be used. The cyclodextrin is one kind of a cyclic oligosaccharide in which D-glucoses are bonded via an α-1,4-glycoside bond to form a cyclic structure, and those in which seven glucoses are bonded are β-cyclodextrin and those in which eight glucoses are bonded are γ-cyclodextrin. The branched β-CD is one in which one or more glucose residues, galactosyl groups or hydroxypropyl groups are linked to β-CD as a side chain, which includes maltosyl β-CD (G2-β-CD), hydroxypropyl-β-CD (HP-β-CD), and the like. Here, the phrase "in the presence of a cyclodextrin" refers to a state in which a cyclodextrin is contained in the cleavage reaction system.

The amount of the cyclodextrin which is present is not particularly limited, and the amount can be preferably from 0.01 to 60% by mass, more preferably from 1 to 50% by mass, and even more preferably from 3 to 40% by mass in the reaction system. When the cyclodextrin is used in two or more kinds, the amount refers to a total amount thereof.

The molar ratio of the cyclodextrin to the sparingly soluble flavonoid having a rhamnoside structure (cyclodextrin/flavonoid) is preferably 0.01 or more, more preferably 0.1 or more, even more preferably 0.9 or more, and even more preferably 1.0 or more, from the viewpoint of efficiency, and the molar ratio is preferably 10.0 or less, more preferably 6.0 or less, even more preferably 4.0 or less, and even more preferably 3.0 or less, from the viewpoint of economic advantages.

As the enzyme having a rhamnosidase activity, origins thereof are not limited, and all derivations such as animal derivation, plant derivation, and microorganism derivation can be used. Further, the enzyme may be a genetically recombinant enzyme. In addition, the form of the enzyme is not particularly limited.

Specific examples of the enzyme having a rhamnosidase activity include hesperiginase, naringinase, β-glucosidase, pectinase and the like.

The amount of the enzyme having a rhamnosidase activity used is varied depending upon the kinds of enzymes used, reaction conditions, the kinds of sparingly soluble flavonoids having a rhamnoside structure of raw materials. When the enzyme is, for example, hesperiginase, naringinase, and β-glucosidase, the amount is preferably from 0.01 to 1,000 U based on 1 g of the sparingly soluble flavonoids having a rhamnoside structure. As to the reaction conditions, the reaction temperature or the pH of the reaction liquid mixture can be selected depending upon the properties of the enzyme used, and the pH is preferably from 3 to 7, and the pH is more preferably from 3.5 to 6.5. In addition, the sparingly soluble flavonoid having a rhamnoside structure can be dissolved at an alkaline region, and then subjected to an enzymatic reaction at a pH of 7 or less. The solvent used in the reaction system includes an aqueous medium. The aqueous medium as used herein refers to water or an aqueous solution of an organic solvent. Examples of water include tap water, distilled water, ion-exchanged water, and purified water. The organic solvent is not particularly limited, so long as the organic solvent is evenly miscible with water. The organic solvent is preferably ethanol, from the viewpoint that the organic solvent is applicable to foods. In addition, the reaction temperature is preferably from 10° to 80° C., and more preferably from 40° to 75° C. In addition, the reaction time is varied depending upon the kinds of the enzymes or the like, and the reaction time can be, for example, from 1 to 100 hours, and preferably from 2 to 24 hours.

The enzyme having a rhamnosidase activity may have a glucosidase activity, and obtainment of an aglycone inclusion compound (a quercetin inclusion compound, a hesperetin inclusion compound, a naringenin inclusion compound, a myricetin inclusion compound or the like) from a sparingly soluble flavonoid having a rhamnoside structure (hesperidin, rutin, naringin, myricitrin or the like) by a glucosidase activity is also not limited, so that these are also embraced in the flavonoid inclusion compound according to the present invention.

The flavonoid inclusion compound formed is an inclusion compound of a flavonoid without a rhamnoside structure and a cyclodextrin, as mentioned above. Here, an inclusion compound refers to a compound formed in such a manner that one chemical species forms a space of a molecular scale and the other chemical species is included in the space by matching the space to the shape and dimensions.

The flavonoid without a rhamnoside structure includes isoquercitrin, quercetin, hesperetin-7-glucoside, hesperetin, naringenin-7-glucoside (prunin), naringenin, luteolin-7-glucoside, diosmetin-7-glucoside, myricetin, eriodictyol-7-glucoside, delphinidin-3-glucoside, cyanidin-3-glucoside, isorhamnetin-3-glucoside, kaempferol-3-glucoside, apigenin-7-rutinoside, acacetin-7-glucoside and the like.

Specific examples of structural formulae of the sparingly soluble flavonoid having a rhamnoside structure and the flavonoid without a rhamnoside structure are shown hereinbelow. The structural formulae of rutin (RTN), hesperidin (HSP) and naringin (NRG), each having a rhamnoside structure, and isoquercitrin (IQC), quercetin (QCT), hesperetin-7-glucoside (HPT-7G), hesperetin (HPT), naringenin-7-glucoside (prunin) (NGN-7G, prunin) and naringenin (NGN), without having a rhamnoside structure are represented by the following formulae.

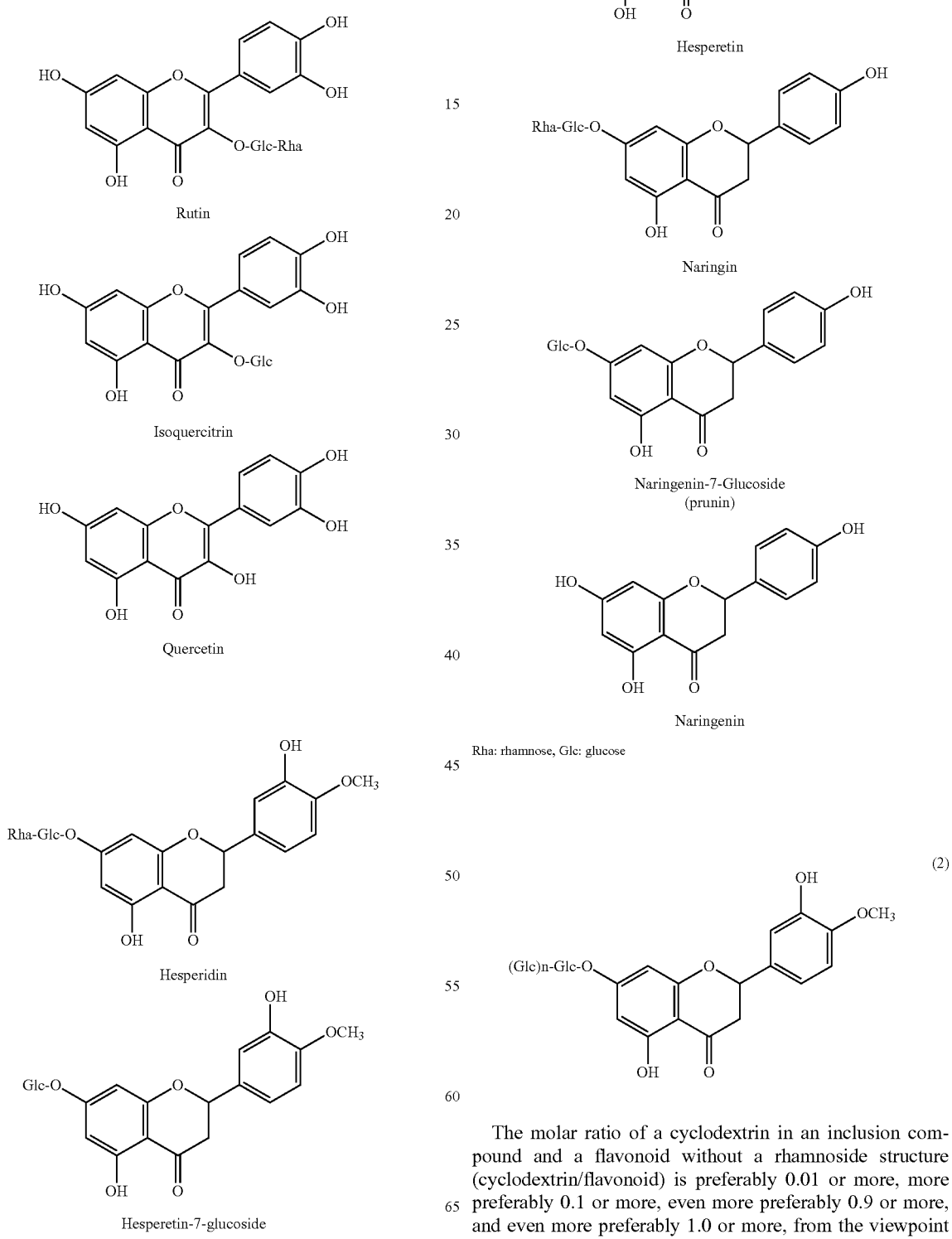

Rha: rhamnose, Glc: glucose

The molar ratio of a cyclodextrin in an inclusion compound and a flavonoid without a rhamnoside structure (cyclodextrin/flavonoid) is preferably 0.01 or more, more preferably 0.1 or more, even more preferably 0.9 or more, and even more preferably 1.0 or more, from the viewpoint of efficiency, and the molar ratio is preferably 10.0 or less, more preferably 6.0 or less, even more preferably 4.0 or less, and even more preferably 3.0 or less, from the viewpoint of economic advantages.

The yield of the flavonoid inclusion compound formed is preferably from 10 to 100%, more preferably from 40 to 100%, more preferably from 70 to 100%, and even more preferably from 90 to 100%. The yield is a percent conversion from a sparingly soluble flavonoid having a rhamnoside structure to a flavonoid without a rhamnoside structure, and the yield can be calculated according to a method described in Examples set forth below. Here, the proportion of the flavonoid inclusion compound formed is not limited, even when the flavonoid inclusion compound formed is a mixture of a raw material flavonoid having a rhamnoside structure (for example, rutin, hesperidin, naringin or the like), or a flavonoid which may be contained in raw materials (for example, quercetin, kaempferol-3-rutinoside, kaempferol-3-glucoside, hesperetin, naringenin and the like), depending upon the flavonoid content or percent conversion of the raw materials used.

In the formed flavonoid inclusion compound or the flavonoid inclusion compound-containing composition described later (both may be collectively referred to as "flavonoid inclusion compound and the like"), a solubility of a flavonoid portion in water may depend on the kinds or the amounts of the sparingly soluble flavonoid having a rhamnoside structure and the cyclodextrin used, and the solubility is preferably 0.01% or more, more preferably 0.015% or more, even more preferably 0.02% or more, even more preferably 1.0% or more, even more preferably 2.0% or more, even more preferably 2.5% or more, and even more preferably 3% or more. Although the upper limit is not particularly limited, the upper limit can be defined as, for example, 20% or less. The solubility of a flavonoid portion in water as used herein is a concentration of percent by mass at 25° C., and the solubility can be measured according to a method described in Examples set forth below.

Specific embodiments will be given hereinbelow.

Embodiment 1-1

A flavonoid inclusion compound containing isoquercitrin included by γ-cyclodextrin, wherein a molar ratio of the isoquercitrin and the γ-cyclodextrin in an inclusion compound (γ-cyclodextrin/isoquercitrin) is preferably from 0.9 to 4.0, and more preferably from 0.9 to 1.8, from the viewpoint of reducing production costs, in which case a solubility of the isoquercitrin in water is preferably 0.01% or more, more preferably 2% or more, even more preferably 2.5% or more, and even more preferably 3% or more.

Embodiment 1-2

A flavonoid inclusion compound containing isoquercitrin included by β-cyclodextrin, wherein a molar ratio of the isoquercitrin and the β-cyclodextrin in an inclusion compound (β-cyclodextrin/isoquercitrin) is from 1.0 to 3.0, in which case a solubility of the isoquercitrin in water is preferably 0.01% or more, more preferably 0.02% or more, even more preferably 0.03% or more, and even more preferably 0.05% or more.

Embodiment 1-3

A flavonoid inclusion compound containing hesperetin-7-glucoside included by a cyclodextrin, wherein a molar ratio of the hesperetin-7-glucoside and the cyclodextrin in an inclusion compound (cyclodextrin/hesperetin-7-glucoside) is from 1.0 to 3.0, in which case a solubility of the hesperetin-7-glucoside in water is preferably 0.01% or more, more preferably 0.02% or more, and even more preferably 0.03% or more.

Embodiment 1-4

A flavonoid inclusion compound containing naringenin-7-glucoside included by β-cyclodextrin, wherein a molar ratio of the naringenin-7-glucoside and the β-cyclodextrin in an inclusion compound (cyclodextrin/naringenin-7-glucoside) is from 1.0 to 3.0, in which case a solubility of the naringenin-7-glucoside in water is preferably 0.01% or more, more preferably 0.02% or more, and even more preferably 0.03% or more.

According to the method for producing a flavonoid inclusion compound of the present invention, in a case of unpurified compound, a flavonoid inclusion compound-containing composition containing a flavonoid inclusion compound and a rhamnose is obtained. In this case, a molar ratio of the flavonoid in the flavonoid inclusion compound and the rhamnose cleaved (rhamnose/flavonoid) is from 0.8 to 1.2.

According to the method for producing a flavonoid inclusion compound of the present invention, in a case where the above yield is not 100%, the inclusion compound would contain a sparingly soluble flavonoid having a rhamnoside structure as an unreacted material. The molar ratio of the flavonoid in the flavonoid inclusion compound and the sparingly soluble flavonoid in the flavonoid inclusion compound-containing composition containing the above unreacted material (sparingly soluble flavonoid/flavonoid in the inclusion compound) is preferably 0.1 or less, more preferably 0.08 or less, and even more preferably 0.05 or less, from the viewpoint of long term stability. The lower limit is not particularly limited, and the lower limit may be 0.001 or more, 0.003 or more, 0.004 or more, and 0.01 or more.

In addition, surprisingly, it has been found that a solubility of a sparingly soluble flavonoid having a rhamnoside structure can be improved by the flavonoid inclusion compound obtained by the production method of the present invention. More specifically, the solubility of a sparingly soluble flavonoid having a rhamnoside structure can be improved by mixing a sparingly soluble flavonoid having a rhamnoside structure with a flavonoid inclusion compound obtained by the production method of the present invention in a medium such that a molar ratio of the flavonoid in the flavonoid inclusion compound to the sparingly soluble flavonoid (flavonoid in inclusion compound/sparingly soluble flavonoid) is preferably from 0.1 to 0.9, more preferably from 0.1 to 0.7, and even more preferably from 0.1 to 0.3. Here, the term in the medium refers to in an aqueous medium, or in an aqueous solution containing food additives such as saccharide, salts, acidulants, sweeteners, flavoring agents, glycerol or propylene glycol, and foods or Chinese herbal medicine such as lemon extracts or Chinese herbal medicine extracts. The method for improving solubility may be carried out by directly using a flavonoid inclusion compound-containing composition containing unreacted materials, or may be carried out by adding a flavonoid inclusion compound or the like to the sparingly soluble flavonoid having a rhamnoside structure. Here, the sparingly soluble flavonoid having a rhamnoside structure and the flavonoid inclusion compound obtained by the production method of the present invention are as mentioned above, which include a combination of, for example, rutin and an isoquercitrin-γ-cyclodextrin inclusion compound, hesperidin and a hesperetin-7-glucoside-β-cyclodextrin inclusion compound, naringin and a narigenin-7-glucoside-β-cyclodextrin inclusion compound, and rutin and a narigenin-7-glucoside-β-cyclodextrin inclusion compound.

The method for producing a flavonoid inclusion compound of the present invention is not particularly limited in carrying out the purification as needed other than a cleaving step, and the purification can be carried out by a resin treatment step (adsorption method, ion-exchanging method and the like), a membrane treatment step (ultrafiltration membrane treatment method, reverse osmosis membrane treatment method, zeta potential membrane treatment method or the like), electrodialysis method, salting out, acid precipitation, recrystallization, solvent fractionation method or the like. For example, the flavonoid inclusion compound-containing composition obtained in the cleaving step is adsorbed with a synthetic porous adsorbent, rhamnose or the like is removed by washing with water, and thereafter the composition is eluted with an alcohol and spray-dried, whereby purified powders can be provided. In addition, after the elution with an alcohol, a diluent or other additives may be contained as components other than the composition. Here, rhamnose or the like can be fractionated and utilized in the fields of foods, medicaments, quasi-drugs, cosmetics, and the like. In addition, a flavonoid alone can be purified from the produced flavonoid inclusion compound produced.

The diluent is not particularly limited so long as the diluent does not impair the effects of the present inventions, and the diluent includes, for example, saccharides such as sugar, glucose, dextrin, starches, trehalose, lactose, maltose, glucose syrup, and liquid sugar; alcohols such as ethanol, propylene glycol, and glycerol; sugar alcohols such as sorbitol, mannitol, xylitol, erythritol, maltitol, reduced glucose syrup, and mannite; or water. In addition, the additives include aids such as phosphates, organic acids, and chelates; antioxidants such as ascorbic acid, and the like.

Next, the method for producing a composition of flavonoid glycosides of the present invention will be described.

The method for producing a composition of flavonoid glycosides of the present invention includes a glycosidation step including treating a flavonoid inclusion compound obtained according to the method of producing a flavonoid inclusion compound of the present invention with a glycosyltransferase to subject the flavonoid inclusion compound to glycosidation. In other words, the method includes a cleaving step including treating a sparingly soluble flavonoid having a rhamnoside structure with an enzyme having an rhamnosidase activity in the presence of a cyclodextrin to cleave rhamnose, and a glycosidation step including treating the flavonoid inclusion compound obtained through the above cleaving step with a glycosyltransferase to subject the flavonoid inclusion compound to glycosidation.

The cleaving step and the flavonoid inclusion compound obtained through the cleaving step are as mentioned above. Here, the phrase obtained through the cleaving step does not intend to exclude methods including steps other than the cleaving step, but also includes ones obtained through optional purification step or the like.

The glycosidation step includes treating a flavonoid inclusion compound obtained through the cleaving step with a glucosyltransferase to subject the flavonoid inclusion compound to glycosidation, to provide a composition of flavonoid glycosides. In addition, the glycosidation step can be carried out while allowing to stand in a solvent such as water, or while stirring, in the same manner as the cleaving step, the air in a headspace in the reaction system may be replaced with an inert gas such as nitrogen in order to prevent oxidation or browning in the reaction, and also an antioxidant such as ascorbic acid can be added to the reaction system. The glycosidation step can be terminated by a known method such as a method including a method of deactivating enzymes by heating or the like.

In the glycosidation step, a cyclodextrin of the flavonoid inclusion compound serves as a sugar donor, and a composition of flavonoid glycosides can be produced, and there are no limitations in additional donations of the sugar donor. Specific examples of the sugar donor that are additionally donated include starch, dextrin, partial hydrolysates of starch such as maltooligosaccharide, xylooligosaccharide, products containing them, and the like.

The glycosyltransferase is not particularly limited, so long as the enzyme has a glycosyltransferase activity against the flavonoid inclusion compound obtained through the cleaving step. As the glycosyltransferase, the origins thereof are not limited, and all derivations such as animal derivation, plant derivation, and microorganism derivation can be used. Further, the enzyme may be a synthetic enzyme by genetically recombinant technique, partial hydrolysis, or the like. In addition, the form of the glycosyltransferase is not particularly limited, and a dried product of an enzyme protein, an enzyme immobilized with an insoluble carrier, a liquid containing an enzyme protein, or the like can be used.

Specific examples of the glycosyltransferase include cyclodextrin glucanotransferase, glucosyltransferase, $\alpha$-glucosidase, $\beta$-glucosidase, $\alpha$-galactosidase, $\beta$-galactosidase, $\alpha$-amylase, xylanase, pullulanase, arabinofuranosidase, and the like.

The amount of the glycosyltransferase used is varied depending upon the kinds of enzymes used, the conditions of glycosylation transfer reactions, the kinds of saccharides, and the like. For example, in a case of cyclodextrin glucanotransferase, the amount used is preferably from 1 to 10,000 U based on 1 g of a flavonoid inclusion compound. When a sparingly soluble flavonoid is subjected to glycosidation, an enzyme reaction is generally carried out in an alkaline region to solubilize a sparingly soluble flavonoid. However, the stability of flavonoid is worsened at an alkaline region of a pH exceeding 7, so that the flavonoid is likely to be decomposed or browned, and further a step of removing browned products and a desalting step by neutralization with an alkali would be required. However, in the flavonoid inclusion compound obtained according to the production method of the present invention, the sparingly soluble flavonoid is solubilized in a high concentration even at a pH of 7 or less, so that an enzyme reaction efficiently processes glycosidation even at a pH of 7 or less. Accordingly, the pH is preferably from 3 to 7, and more preferably from 6 to 6.8, from the viewpoint of production efficiency or quality. However, the glycosylation transfer can be carried out in an alkaline region, or the glycosylation transfer can be carried out by a pH adjustment to an alkaline region, followed by adjustment to a pH of 7 or less. The solvent used in the reaction system includes an aqueous medium. Also, the reaction temperature is preferably from 40° to 70° C., and more preferably from 50° to 65° C. In addition, the reaction time is varied depending upon the kinds of enzymes and the like, and the reaction time can be, for example, from 0.5 to 120 hours, and preferably from 1 to 30 hours. In addition, it is preferable that after the cleaving step, the temperature and the pH are continuously changed to optimal conditions, and a glycosyltransferase is added thereto to carry out the glycosidation step, from the viewpoint of production efficiency.

The binding manner of saccharides to a flavonoid may be either one of an $\alpha$-bond or a $\beta$-bond. The kinds of saccharides to be bonded are not particularly limited, and one or more members selected from pentoses and hexoses such as glucose, galactose and fructose are preferred. In addition, the number of bonds of saccharides is preferably from 1 to 30, more preferably from 1 to 25, even more preferably from 1 to 20, even more preferably from 1 to 15, and even more preferably from 1 to 10. The composition of flavonoid glycosides refers to ones containing a mixture of glycosides in which the above saccharides are bonded to a flavonoid, and the proportion of the number of bonds of each glycoside is not limited, and the following embodiments are preferred, from the viewpoint of not impairing the flavor of foodstuff or the like.

Embodiment 2-1

A composition of isoquercitrin glycosides containing a compound represented by the following general formula (1):

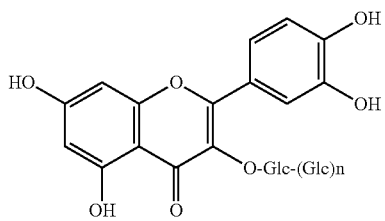

(1)

where in the general formula (1), Glc means a glucose residue, and n means an integer of 0 or 1 or more, and wherein the content of glycosides having n=0 is 10% by mol or more and 30% by mol or less, the content of glycosides having n=1 to 3 is 50% by mol or less, and the content of glycosides having n=4 or more is 30% by mol or more, of the above composition of glycosides. Preferably, the content of glycosides having n=0 is 10% by mol or more and 30% by mol or less, the content of glycosides having n=1 to 3 is 35% by mol or more and 45% by mol or less, and the content of glycosides having n=4 or more is 30% by mol or more and 50% by mol or less.

Embodiment 2-2

A composition of glycosides of hesperetin-7-glucoside containing a compound represented by the following general formula (2):

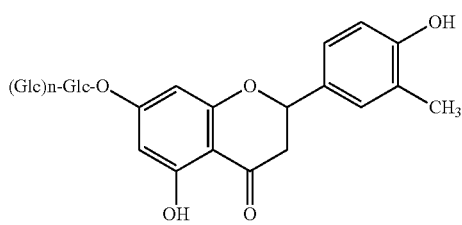

(2)

where in the general formula (2), Glc means a glucose residue, and n means an integer of 0 or 1 or more, and wherein the content of glycosides having n=0 is 10% by mol or more and 30% by mol or less, the content of glycosides having n=1 to 3 is 50% by mol or less, and the content of glycosides having n=4 or more is 30% by mol or more, of the above composition of glycosides. Preferably, the content of glycosides having n=0 is 10% by mol or more and 25% by mol or less, the content of glycosides having n=1 to 3 is 35% by mol or more and 50% by mol or less, and the content of glycosides having n=4 or more is 30% by mol or more and 50% by mol or less.

Embodiment 2-3

A composition of glycosides of naringenin-7-glucoside containing a compound represented by the following general formula (3):

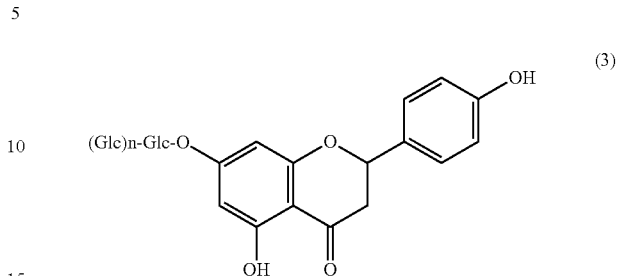

(3)

where in the general formula (3), Glc means a glucose residue, and n means an integer of 0 or 1 or more, and wherein the content of glycosides having n=0 is 10% by mol or more and 30% by mol or less, the content of glycosides having n=1 to 3 is 50% by mol or less, and the content of glycosides having n=4 or more is 30% by mol or more, of the above composition of glycosides.

Here, the number of bonds of a glucose group (n number) can be optionally adjusted. For example, after forming a composition of flavonoid glycosides, the number of glucose sugar chains in the molecule of the composition of flavonoid glycosides can be reduced by carrying out the treatment with various amylases (α-amylase, β-amylase, glucoamylase, α-glucosidase, and the like) alone or in a combination thereof, to provide a composition of flavonoid glycosides having an optional glucose sugar chain length.

The method for producing a composition of flavonoid glycosides of the present invention is not particularly limited in carrying out the purification as needed other than the cleaving step and the glycosidation step, and the purification can be carried out by a resin treatment step (adsorption method, ion-exchanging method and the like), a membrane treatment step (ultrafiltration membrane treatment method, reverse osmosis membrane treatment method, zeta potential membrane treatment method or the like), electrodialysis method, salting out, acid deposition, recrystallization, solvent fractionation method or the like. For example, the composition of flavonoid glycosides obtained in the glycosidation step is adsorbed with a synthetic porous adsorbent to adsorb the composition of glycosides, washed with water, eluted with an alcohol, and thereafter spray-dried, to provide purified powders. In addition, after the elution with an alcohol, a diluent or other additives may be contained as components other than the composition.

Specific examples of the diluent are the same as the ones listed in the method for producing a flavonoid inclusion compound.

The solubility of the composition of flavonoid glycosides obtained according to the production method of the present invention in water, calculated as a flavonoid, is preferably 0.01% or more, more preferably 0.015% or more, even more preferably 0.02% or more, even more preferably 0.1% or more, and even more preferably 0.5% or more. The upper limit is not particularly limited, and the upper limit can be defined as, for example, 20% or less.

The flavonoid inclusion compound and the composition of flavonoid glycosides obtained according to the production method of the present invention can be provided in the form of food for which bioavailability is sustainably improved by a combination with a sparingly soluble flavonoid having a rhamnoside structure which is said to have a delayed bioavailability or a composition of flavonoid glycosides having a rhamnoside structure. Combinations, for example, include a combination of an isoquercitrin inclusion compound and rutin, a combination of a composition of isoquercitrin glycosides and a composition of rutin glycosides (for example, αG Rutin, Toyo Sugar Refining Co., Ltd.), a combination of a hesperetin-7-glucoside inclusion compound and a composition of hesperidin glycosides (for example, αG Hesperidin, Toyo Sugar Refining Co., Ltd.), and a combination of a composition of glycosides of hesperetin-7-glucoside and a composition of hesperidin glycosides (for example, Monoglycosyl Hesperidin, HAYASHIBARA CO., LTD.).

In addition, the composition of flavonoid glycosides obtained according to the production method of the present invention is combined with another sparingly soluble flavonoid, whereby a solubility of the other sparingly soluble flavonoid can be improved. Combinations are, for example, a combination of a composition of isoquercitrin glycosides and rutin, a combination of a composition of glycosides of hesperetin-7-glucoside and hesperidin, and a combination of a composition of glycosides of hesperetin-7-glucoside and myricitrin. In addition, the molar ratio thereof (composition of glycosides/other sparingly soluble flavonoid) is preferably from 0.1 to 0.5, more preferably from 0.1 to 0.3, and even more preferably from 0.1 to 0.15.

The flavonoid inclusion compound and/or the composition of flavonoid glycosides obtained according to the production method of the present invention is excellent in the body absorption rate, and additionally excellent in prevention of fading, prevention of deterioration in flavors, and storage stability, so that the flavonoid inclusion compound and/or the composition of flavonoid glycosides can be suitably used as a composition for foods, a composition for medicaments, a composition for cosmetics and a composition for foods additives. More specifically, the flavonoid inclusion compound and/or the composition of flavonoid glycosides can be used as a material for anti-allergy, anti-oxidation, anticancer, anti-inflammation, improvement in intestinal flora, deodorization, suppression of plasma cholesterol elevation, suppression of blood pressure elevation, suppression of blood sugar level elevation, suppression of platelet aggregation, prevention of dementia, combustion of body fat, suppression of body fat accumulation, improvement in staying power, anti-fatigue, improvement in sensitivity to cold, improvement of skin conditions, hair restoration, suppression of amyotrophy, or sleeping, and also used as an antioxidant, fading preventive, deterioration preventive for flavor for food additives. The composition for foods additives is added for prevention of deterioration of a sweetener, a colorant, a preservative, a thickening stabilizer, a color developing agent, a bleaching agent, a mildewproof agent, a gum base, a bittering agent, a lustering agent, an acidulant, a seasoning, an emulsifying agent, a reinforcing agent, an agent for production, a flavor, or the like, and can be provided in the form of a mixed formulation. In other words, the present invention can provide foodstuff, medicaments, cosmetics and the like, each containing a flavonoid inclusion compound and/or a composition of flavonoid glycosides obtained according to the production method of the present invention.

The foodstuff include foods and beverages, which include, for example, nutrient supplements, health foods, foods for specified health use, foods with function claims, foods for diet therapy, comprehensive health foods, supplements, tea beverages, coffee beverages, juices, refreshing beverages, health drinks, and the like.

The medicament includes drugs or quasi-drugs, and the medicaments are preferably oral formulations or dermally externally applicable agents, and can be in the form of solution, tablet, granule, capsule, syrup, lotion, spray, or ointment.

The cosmetics can be in the form of cream, liquid lotion, milky emulsion lotion, or spray.

The amount of the flavonoid inclusion compound and/or the composition of flavonoid glycosides blended in the foodstuff, medicament or cosmetics of the present invention is not particularly limited, and the amount blended can be properly designed, with reference to a preferred daily ingestion amount of flavonoids, taking into consideration the solubility, tastiness or the like. For example, the amount of the flavonoid inclusion compound and/or the composition of flavonoid glycosides obtained according to the production method of the present invention blended in the composition for foods as a flavonoid portion can be preferably from 0.001 to 30% by mass, more preferably from 0.01 to 20% by mass, and even more preferably from 0.02 to 10% by mass, and the amount blended in the composition for foods can be determined such that the flavonoid inclusion compound and/or the composition of flavonoid glycosides can be ingested in an amount of preferably from 10 mg to 20 g, more preferably from 30 mg to 10 g, and even more preferably from 100 mg to 5 g per day at once or divided into plural times (for example, three times). In addition, the amount of the flavonoid inclusion compound and/or the composition of flavonoid glycosides blended to the food additive formulation can be used in an amount of preferably from 0.001 to 50% by mass, more preferably from 0.01 to 40% by mass, and even more preferably from 0.1 to 30% by mass as a volume at which the flavonoids exhibit effects.

EXAMPLES

The present invention will be more specifically described hereinbelow by way of Examples, without intending to limit the scope of the present invention to these Examples. Here, "%" means "% by mass," unless noted otherwise particularly.

Preparation of Flavonoid Inclusion Compound-Containing Composition

Examples 1 to 31

To a 1,000 ml beaker were added a sparingly soluble flavonoid having a rhamnoside structure (rutin or hesperidin) and a cyclodextrin as listed in Table 1 or 2, and water was added thereto to make up a mass of 1,000 g. The liquid mixture was adjusted to 70° C. and a pH of 4. Thereafter, 3 to 30 g of a naringinase (Amano Enzyme Inc., 155 u/g) was added thereto while stirring, and a reaction mixture was reacted for 24 hours. The temperature was set back to room temperature, and the mixture was filtered with a filter paper, to give an inclusion compound of a flavonoid without a rhamnoside structure (isoquercitrin or hesperetin-7-glucoside) and a cyclodextrin, and a flavonoid inclusion compound-containing composition containing a cleaved rhamnose.

Comparative Examples 1 to 3

Each of compositions of Comparative Examples 1 and 3 was prepared in the same manner as Examples 16 and 17, except that a cyclodextrin was not added. In addition, a composition of Comparative Example 2 was prepared in the same manner as Example 16, except that a dextrin was added in place of a cyclodextrin.

Comparative Example 101

To a 100 ml beaker were added isoquercitrin and γ-cyclodextrin as listed in Table 1-2, each of which was prepared as follows, and water was added thereto up to make up a mass of 100 g. The liquid mixture was stirred for 24 hours at 70° C. and a pH of 4.5. The temperature was then set back to room temperature, and the mixture was filtered with a filter paper, to give a composition containing an inclusion compound of isoquercitrin and γ-cyclodextrin.

Preparation of Isoquercitrin

Ten grams of rutin used in Table 1 was added to make 100 L of an aqueous solution, and the solution was adjusted to 70° C. and a pH of 4.5. Thereafter, 1 g of a naringinase (Amano Enzyme Inc., 155 u/g) was added thereto while stirring the solution, and the liquid mixture was recovered and dried, to give 7.2 g of isoquercitrin having a content of 96% or more. It was confirmed that the product was identical to a reagent isoquercitrin (Wako) by HPLC.

Examples 101 to 109

Each of a composition containing an inclusion compound of naringenin-7-glucoside and β-cyclodextrin was prepared in the same manner as Examples 1 to 31 except that raw materials listed in Table 2-2 were used.

Comparative Example 102

A composition of Comparative Example 102 was prepared in the same manner as Example 104 except that a cyclodextrin was not added.

The details used in Tables 1, 1-2, 2 and 2-2 are shown hereinbelow. RTN: Rutin prepared as follows.

Fifty kilograms of buds of *Sophora* belonging to *Fabaceae* were immersed in 500 L of hot water for 3 hours, and a filtrate was then obtained after filtration. Thereafter, the filtrate was cooled to room temperature, and the precipitated components were separated by filtration. The precipitates were washed with water, recrystallized and dried, to give 3,190 g of rutin having a content of 96% or more. It was confirmed that the product had identical peaks to those of a reagent rutin (Wako) by HPLC.

HSP: Hesperidin (content: 97% or more, manufactured by Hamari Chemicals., Ltd.)
NRG: Naringin (content: 95% or more, manufactured by SIGMA)
β-CD: β-Cyclodextrin (manufactured by PEARL ACE CORPORATION)
γ-CD: γ-Cyclodextrin (manufactured by PEARL ACE CORPORATION)
Dextrin: Sandec#70 (manufactured by Sanwa Starch Co., Ltd.)

Percent Conversion from Rutin to Isoquercitrin

The reaction-terminated liquid mixtures before filtration of Examples 1 to 16 and Comparative Examples 1 and 2 were used as measurement samples. From an areal ratio according to HPLC (SHIMADZU) (peak area of isoquercitrin/peak area of rutin) under<the conditions of HPLC:
Column: CAPCELL PAK C18, SIZE 4.6 mm×250 mm (SHISEIDO),
Eluent: 20% (v/v) acetonitrile/0.1% aqueous phosphoric acid solution,
Detection: 351 nm,
Flow rate: 0.4 ml/min,
Column temperature: 70° C.>,
a percent conversion was calculated as follows:

percent conversion (%)=peak area of isoquercitrin× 100/(peak area of rutin+peak area of isoquercitrin).

It was confirmed that the isoquercitrin had identical peaks to those of a reagent isoquercitrin (Wako) by HPLC. All the percent conversions of Examples 1 to 16 were 96% or more. On the other hand, the percent conversion of Comparative Example 1 was as low as 56% and the percent conversion of Comparative Example 2 was as low as 57%, as compared to Example 16 with the same amount of the enzyme.

Percent Conversion from Hesperidin to Hesperetin-7-Glucoside

The reaction-terminated liquid mixtures before filtration of Examples 17 to 31 and Comparative Example 3 were used as measurement samples. From an areal ratio according to HPLC (SHIMADZU) (peak area of hesperetin-7-glucoside/peak area of hesperidin) under<the conditions of HPLC:
Column: CAPCELL PAK C18, SIZE 4.6 mm×250 mm (SHISEIDO),
Eluent: 40% (v/v) acetonitrile/0.1% aqueous phosphoric acid solution,
Detection: 280 nm,
Flow rate: 0.4 ml/min,
Column temperature: 70° C.>,
a percent conversion was calculated as follows:

a percent conversion (%)=peak area of hesperetin-7-glucoside×100/(peak area of rutin+peak area of hesperetin-7-glucoside).

It was confirmed that the hesperetin-7-glucoside had identical peaks to those of a dried product which was confirmed to be hesperetin-7-glucoside by NMR. All the percent conversions of Examples 17 to 31 were 96% or more. On the other hand, the percent convention of Comparative Example 3 was as low as 57%.

Percent Conversion from Naringin to Naringenin-7-Glucoside

The reaction-terminated liquid mixtures before filtration of Examples 101 to 109 and Comparative Example 102 were used as measurement samples. From an areal ratio according to HPLC (SHIMADZU) (peak area of naringenin-7-glucoside/peak area of naringin) under<the conditions of HPLC:
Column: CAPCELL PAK C18, SIZE 4.6 mm×250 mm (SHISEIDO),
Eluent: 25% (v/v) acetonitrile/0.1% aqueous phosphoric acid solution,
Detection: 280 nm,
Flow rate: 0.4 ml/min,
Column temperature: 70° C.>,
a percent conversion was calculated.
Specifically, a percent conversion was calculated as follows:

percent conversion (%)=peak area of naringenin-7-glucoside×100/(peak area of naringin+peak area of naringenin-7-glucoside).

It was confirmed that the naringenin-7-glucoside had identical peaks to those of a reagent naringenin-7-glucoside (Wako) by HPLC. The percent conversions of Examples 101 to 109 and Comparative Example 102 were 95% or more.

Isoquercitrin (IQC) Concentration (Absorptiometric Analysis)

Reaction-terminated liquid mixtures of Examples 1 to 16 and Comparative Examples 1, 2 and 101 were allowed to stand at room temperature, and 1 ml of supernatant was then filtered to be used as measurement samples. A calibration curve was drawn at an absorbance of 351 nm (0.1% phosphoric acid solution) using a reagent rutin (Wako), a rutin concentration was then calculated from the absorbance of the measurement samples, a value calculated by compensating with a percent and multiplying the product with a factor of 0.761 (molecular weight ratio of isoquercitrin/rutin (464.38/610.52=0.761)) was obtained as an isoquercitrin concentration. The results are shown in Table 1 and 1-2. Here, the percent conversion at the time of concentration calculation was calculated after subjecting the same samples as those for the concentration analysis to HPLC determination.

Hesperetin-7-Glucoside (HPT-7G) Concentration (Absorptiometric Analysis)

Reaction-terminated liquid mixtures of Examples 17 to 31 and Comparative Example 3 were allowed to stand at room temperature, and 1 ml of supernatant was then filtered to be used as measurement samples. A calibration curve was drawn at an absorbance of 280 nm (0.1% phosphoric acid solution) using a reagent hesperidin (Wako), a hesperidin concentration was then calculated from the absorbance of the measurement samples, and a value calculated by compensating with a percent conversion according to HPLC analysis, and multiplying the product by a factor of 0.761 (molecular weight ratio of hesperetin-7-glucoside/hesperidin (464.42/610.56=0.761)) was obtained as a hesperetin-7-glucoside concentration. The results are shown in Table 2. Here, the percent conversion at the time of concentration calculation was calculated after subjecting the same samples as those for the concentration analysis to HPLC measurement.

Naringenin-7-Glucoside (NGN-7G) Concentration (Absorptiometric Analysis)

Reaction-terminated liquid mixtures of Examples 101 to 109 and Comparative Example 102 were allowed to stand at room temperature, and 1 ml of supernatant was then filtered to be used as measurement samples. A calibration curve was drawn at an absorbance of 280 nm (0.1% phosphoric acid solution) using a reagent naringin (manufactured by SIGMA, hereinafter, NRG), a naringin concentration was then calculated from the absorbance of the measurement samples, and a value calculated by compensating with a percent conversions according to HPLC analysis, and multiplying the product by a factor of 0.748 (ratio of molecular weight of naringin/naringenin-7-glucoside (434.39/580.54=0.748)) was obtained as a naringenin-7-glucoside concentration. The results are shown in Table 2-2. Here, the percent conversion at the time of concentration calculation was calculated after subjecting the same samples as ones for the concentration analysis to HPLC determination.

Molar Ratio (CD/IQC (Molar Ratio), CD/HPT-7G (Molar Ratio), and CD/NGN-7G (Molar Ratio)) (HPLC Saccharide Analysis)

Reaction-terminated liquid mixtures of Examples 1 to 31 and 101 to 109, and Comparative Example 101 were allowed to stand at room temperature, and 1 ml of supernatant was then filtered to be used as measurement samples. A calibration curve is drawn with β-cyclodextrin (Wako) and γ-cyclodextrin (Wako), according to HPLC (SHIMADZU) analysis under<Conditions of HPLC:
Column: Inertsil $NH_2$ (4.6×150 mm (GL Science Inc.),
Eluent: 65% acetonitrile/water (v/v),
Detection: differential refractometer, RID-10A (SHIMADZU),
Flow rate: 1 ml/min,
Column temperature: 40° C.>, and
a molar concentration of cyclodextrin of samples was then calculated, and a molar ratio of cyclodextrin/isoquercitrin, cyclodextrin/hesperetin-7-glucoside and cyclodextrin/naringenin-7-glucoside was calculated with a molar concentration of isoquercitrin, hesperetin-7-glucoside and naringenin-7-glucoside. The results are shown in Tables 1, 1-2, 2 and 2-2. Here, the molar ratio of the filtrate after the termination of the reaction was same in the case of lyophilized products.

Solubility (IQC Solubility, HPT-7G Solubility and NGN-7G Solubility)

Reaction-terminated liquid mixtures of Examples 1 to 31 and 101 to 109, and Comparative Examples 1 to 3, 101 and 102 were allowed to stand at room temperature, then filtered and lyophilized to give dried products. The dried products prepared above were added to a 100 ml beaker containing 50 ml of water at 50° C. with stirring until the dried products were no longer dissolved and precipitated out. The liquid mixture was allowed to stand at room temperature (25° C.), 1 ml of the supernatant was then filtered, and an isoquercitrin concentration, a hesperetin-7-glucoside concentration and a naringenin-7-glucoside concentration were calculated according to absorptiometric analysis, to obtain solubility. However, when the amount of the dried products was insufficient at the time of determination of solubility, the same example experimentations were repeatedly carried out to obtain the required amount, and the solubility was measured. In addition, it was confirmed with a differential-scanning calorimeter (DSC), nuclear magnetic resonance (NMR) and a Fourier transform-infrared spectrophotometer (FT-IR) that in Examples 1 to 31 and 101 to 109, and Comparative Example 101 a flavonoid was included with a cyclodextrin. The results of the solubility are shown in Tables 1, 1-2, 2 and 2-2. Here, the lyophilized products of the flavonoid inclusion compounds in which rhamnose was removed by dialysis of the filtrate at room temperature after the termination of the reaction in Examples 1 to 31 and 101 to 109 also showed nearly the same levels of solubility.

TABLE 1

| | (1) RTN (% by mass) | (2) β-CD (% by mass) | (3) γ-CD (% by mass) | (4) Dextrin (% by mass) | (5) CD/RTN (molar ratio) | (6) IQC Conc. (% by mass) | (7) CD/IQC (molar ratio) | (8) IQC Solubility (% by mass) |
|---|---|---|---|---|---|---|---|---|
| Ex. 1 | 2.0 | 5.6 | 0 | 0 | 1.5 | 1.5 | 1.5 | 1.6 |
| Ex. 2 | 2.0 | 7.4 | 0 | 0 | 2.0 | 1.6 | 2.0 | 1.1 |
| Ex. 3 | 3.0 | 11.2 | 0 | 0 | 2.0 | 2.4 | 1.9 | 1.0 |
| Ex. 4 | 3.0 | 16.7 | 0 | 0 | 3.0 | 2.3 | 3.0 | 0.8 |
| Ex. 5 | 4.0 | 14.9 | 0 | 0 | 2.0 | 3.0 | 2.0 | 1.2 |
| Ex. 6 | 4.0 | 22.3 | 0 | 0 | 3.0 | 3.1 | 2.9 | 0.8 |
| Ex. 7 | 4.0 | 0.15 | 0 | 0 | 0.02 | 0.03 | 2.0 | 1.1 |
| Ex. 8 | 4.0 | 0 | 0.08 | 0 | 0.01 | 0.03 | 1.0 | 9.9 |

TABLE 1-continued

|  | (1) RTN (% by mass) | (2) β-CD (% by mass) | (3) γ-CD (% by mass) | (4) Dextrin (% by mass) | (5) CD/RTN (molar ratio) | (6) IQC Conc. (% by mass) | (7) CD/IQC (molar ratio) | (8) IQC Solubility (% by mass) |
|---|---|---|---|---|---|---|---|---|
| Ex. 9 | 4.0 | 0 | 7.6 | 0 | 0.9 | 3.0 | 0.9 | 10.2 |
| Ex. 10 | 4.0 | 0 | 8.5 | 0 | 1.0 | 3.0 | 1.0 | 10.2 |
| Ex. 11 | 4.0 | 0 | 12.7 | 0 | 1.5 | 3.0 | 1.5 | 8.9 |
| Ex. 12 | 4.0 | 0 | 15.3 | 0 | 1.8 | 3.1 | 1.8 | 7.7 |
| Ex. 13 | 4.0 | 0 | 17.0 | 0 | 2.0 | 3.1 | 2.0 | 6.4 |
| Ex. 14 | 4.0 | 0 | 25.4 | 0 | 3.0 | 3.0 | 3.0 | 4.2 |
| Ex. 15 | 4.0 | 0 | 33.9 | 0 | 4.0 | 3.1 | 4.0 | 3.2 |
| Ex. 16 | 8.0 | 0 | 17.0 | 0 | 1.0 | 6.2 | 1.0 | 9.6 |
| Comp. Ex. 1 | 8.0 | 0 | 0 | 0 | — | 0.01 | — | 0.01 |
| Comp. Ex. 2 | 8.0 | 0 | 0 | 17.0 | — | 0.01 | — | 0.01 |

Notes of Table 1
(1) Rutin concentration at the time of the beginning of the reaction (% by mass)
(2) β-Cyclodextrin concentration at the time of the beginning of the reaction (% by mass)
(3) γ-Cyclodextrin concentration at the time of the beginning of the reaction (% by mass)
(4) Dextrin concentration at the time of the beginning of the reaction (% by mass)
(5) Cyclodextrin/rutin at the time of the beginning of the reaction (molar ratio)
(6) Isoquercitrin concentration of the filtrate after the termination of the reaction (% by mass)
(7) Cyclodextrin/isoquercitrin of the filtrate after the termination of the reaction (molar ratio)
(8) Isoquercitrin solubility of the lyophilized product of the filtrate after the termination of the reaction (% by mass)

TABLE 1-2

|  | (11) IQC (% by mass) | (12) γ-CD (% by mass) | (13) CD/IQC (molar ratio) | (14) IQC Conc. (% by mass) | (15) CD/IQC (molar ratio) | (16) IQC Solubility (% by mass) |
|---|---|---|---|---|---|---|
| Comp. Ex. 101 | 3.0 | 8.4 | 1.0 | 0.36 | 8.4 | 0.8 |

Notes of Table 1-2
(11) Isoquercitrin concentration at the time of the beginning of heating while stirring (% by mass)
(12) γ-Cyclodextrin concentration at the time of the beginning of heating while stirring (% by mass)
(13) Cyclodextrin/isoquercitrin at the time of the beginning of heating while stirring (molar ratio)
(14) Isoquercitrin concentration of the filtrate after heating while stirring (% by mass)
(15) Cyclodextrin/isoquercitrin of the filtrate after heating while stirring (molar ratio)
(16) Isoquercitrin solubility of the lyophilized product of the filtrate after heating while stirring (% by mass)

As clear from Table 1, it could be seen that an inclusion compound of isoquercitrin and a cyclodextrin can be efficiently obtained together with the cleavage reaction of rhamnose from rutin according to the production method of the present invention. On the other hand, Comparative Examples 1 and 2 had low percent conversions and also low solubilities. Here, the reaction liquid mixtures and the reaction-terminated liquid mixtures of Examples 7 and 8 and Comparative Examples 1 to 3 were in a suspended state. However, the reaction liquid mixtures of Examples 1 to 6 and 9 to 16 were in a suspended state at an early stage of the reaction and a medium stage of the reaction, but the reaction liquid mixtures were dissolved at the time of termination of the reaction and the subsequent time of allowing the reaction liquid mixtures to stand at room temperature. Therefore, the inclusion percent of an isoquercitrin-cyclodextrin inclusion compound (isoquercitrin concentration in an inclusion compound (concentration of filtrate that is allowed to stand at room temperature after the termination of the reaction)×100/ isoquercitrin concentration in the reaction-terminated liquid mixture (liquid mixture before filtration)) was nearly 100%. However, as Comparative Example 101 of Table 1-2, mere mixing and heating of isoquercitrin and γ-cyclodextrin of the same composition as Example 10 would always be in a suspended state from the beginning to the end of the reaction, and the inclusion ratio (isoquercitrin concentration in an inclusion compound (concentration of filtrate that is allowed to stand at room temperature after the termination of the reaction)×100/isoquercitrin concentration in the reaction-terminated liquid mixture (liquid mixture before filtration)) was also as low as 12%, and also solubility of the lyophilized product of the filtrate was low.

TABLE 2

|  | (21) HSP (% by mass) | (22) β-CD (% by mass) | (23) γ-CD (% by mass) | (24) CD/HSP (molar ratio) | (25) HPT-7G Conc. (% by mass) | (26) CD/ HPT-7G (molar ratio) | (27) HPT-7G Solubility (% by mass) |
|---|---|---|---|---|---|---|---|
| Ex. 17 | 3.0 | 0.08 | 0 | 0.01 | 0.022 | 1.5 | 3.5 |
| Ex. 18 | 3.0 | 7.3 | 0 | 1.3 | 2.3 | 1.3 | 3.8 |
| Ex. 19 | 3.0 | 8.4 | 0 | 1.5 | 2.3 | 1.5 | 3.6 |
| Ex. 20 | 3.0 | 11.2 | 0 | 2.0 | 2.3 | 2.0 | 2.8 |
| Ex. 21 | 3.0 | 16.7 | 0 | 3.0 | 2.3 | 3.0 | 2.0 |
| Ex. 22 | 4.0 | 11.2 | 0 | 1.5 | 2.9 | 1.6 | 3.5 |
| Ex. 23 | 4.0 | 14.9 | 0 | 2.0 | 3.0 | 2.0 | 2.7 |
| Ex. 24 | 2.0 | 0 | 6.4 | 1.5 | 1.4 | 1.6 | 4.0 |
| Ex. 25 | 2.0 | 0 | 8.5 | 2.0 | 1.6 | 1.9 | 3.8 |

TABLE 2-continued

|  | (21) HSP (% by mass) | (22) β-CD (% by mass) | (23) γ-CD (% by mass) | (24) CD/HSP (molar ratio) | (25) HPT-7G Conc. (% by mass) | (26) CD/ HPT-7G (molar ratio) | (27) HPT-7G Solubility (% by mass) |
|---|---|---|---|---|---|---|---|
| Ex. 26 | 4.0 | 0 | 0.08 | 0.01 | 0.015 | 2.0 | 3.7 |
| Ex. 27 | 4.0 | 0 | 12.7 | 1.5 | 3.1 | 1.5 | 4.2 |
| Ex. 28 | 4.0 | 0 | 17.0 | 2.0 | 2.9 | 2.1 | 3.7 |
| Ex. 29 | 5.0 | 0 | 15.9 | 1.5 | 3.7 | 1.5 | 4.1 |
| Ex. 30 | 5.0 | 0 | 21.2 | 2.0 | 3.9 | 1.9 | 3.8 |
| Ex. 31 | 5.0 | 0 | 31.8 | 3.0 | 3.8 | 3.0 | 2.7 |
| Comp. Ex. 3 | 3.0 | 0 | 0 | — | 0.007 | — | 0.007 |

Notes of Table 2
(21) Hesperidin concentration at the time of the beginning of the reaction (% by mass)
(22) β-Cyclodextrin concentration at the time of the beginning of the reaction (% by mass)
(23) γ-Cyclodextrin concentration at the time of the beginning of the reaction (% by mass)
(24) Cyclodextrin/hesperidin at the time of the beginning of the reaction (molar ratio)
(25) Hesperetin-7-glucoside concentration of the filtrate after the termination of the reaction (% by mass)
(26) Cyclodextrin/hesperetin-7-glucoside of the filtrate after the termination of the reaction (molar ratio)
(27) Hesperetin-7-glucoside solubility of the lyophilize product of the filtrate after the termination of the reaction (% by mass)

As is clear from Table 2, it could be seen that an inclusion compound of hesperetin-7-glucoside and a cyclodextrin was efficiently obtained together with the cleavage reaction of rhamnose from hesperidin according to the production method of the present invention. On the other hand, Comparative Example 3 had a low percent conversion and also a low solubility. Here, the reaction liquid mixtures and the reaction-terminated liquid mixtures of Examples 17 and 26, and Comparative Example 3 were in a suspended state. However, the reaction liquid mixtures of Examples 18 to 25, and Examples 27 to 31 were in a suspended state at an early stage of the reaction and a medium stage of the reaction, but the reaction liquid mixtures were dissolved at the time of termination of the reaction and at the time when the liquid mixture was allowed to stand at room temperature. Also, the inclusion percent in which a hesperetin-7-glucoside-cyclodextrin inclusion compound was formed (hesperetin-7-glucoside concentration in the inclusion compound (concentration of the filtrate that is allowed to stand at room temperature after the termination of the reaction)×100/hesperetin-7-glucoside concentration of reaction-terminated liquid (liquid mixture before filtration)) was nearly 100%.

TABLE 2-2

|  | (31) NRG (% by mass) | (32) β-CD (% by mass) | (33) CD/ NRG (molar ratio) | (34) NGN-7G Conc. (% by mass) | (35) CD/ NGN-7G (molar ratio) | (36) NGN-7G Solubility (% by mass) |
|---|---|---|---|---|---|---|
| Ex. 101 | 1.0 | 2.0 | 1.0 | 0.75 | 1.0 | 10.1 |
| Ex. 102 | 1.0 | 3.9 | 2.0 | 0.75 | 2.0 | 5.5 |
| Ex. 103 | 1.0 | 5.9 | 3.0 | 0.75 | 3.0 | 3.7 |
| Ex. 104 | 2.0 | 3.9 | 1.0 | 1.5 | 1.0 | 10.6 |
| Ex. 105 | 2.0 | 7.8 | 2.0 | 1.5 | 2.0 | 5.2 |
| Ex. 106 | 2.0 | 11.8 | 3.0 | 1.5 | 3.0 | 3.5 |
| Ex. 107 | 4.0 | 7.8 | 1.0 | 3.0 | 1.0 | 10.5 |
| Ex. 108 | 5.0 | 9.8 | 1.0 | 3.7 | 1.0 | 10.3 |
| Ex. 109 | 6.0 | 11.8 | 1.0 | 4.5 | 1.0 | 10.7 |
| Comp. Ex. 102 | 2.0 | 0 | 0 | 0.3 | 0 | 0.2 |

Notes of Table 2-2
(31) Naringin concentration at the time of the beginning of the reaction (% by mass)
(32) β-Cyclodextrin concentration at the time of the beginning of the reaction (% by mass)
(33) Cyclodextrin/naringin at the time of the beginning of the reaction (molar ratio)
(34) Naringenin-7-glucoside concentration of the filtrate after the termination of the reaction (% by mass)
(35) Cyclodextrin/naringenin-7-glucoside of the filtrate after the termination of the reaction (molar ratio)
(36) Naringenin-7-glucoside solubility of the lyophilized product of the filtrate after termination of the reaction (% by mass)

As clear from Table 2-2, according to the production method of the present invention, an inclusion compound of naringenin-7-glucoside and βcyclodextrin was efficiently obtained together with the cleavage reaction of rhamnose from naringin, and also the solubility was improved. Although Comparative Example 102 had a percent conversion of 95% or more, since precipitates were formed immediately after the liquid mixture was allowed to stand at room temperature after the termination of the reaction, the solubility was low. However, after the termination of the reactions of Examples 101 to 109, the filtrates that were allowed to stand at room temperature were dissolved, and the inclusion percent in which a naringenin-7-glucoside-cyclodextrin inclusion compound was formed (naringenin-7-glucoside concentration in the inclusion compound (concentration of the filtrate that is allowed to stand at room temperature after the termination of the reaction)×100/naringenin-7-glucoside concentration of the reaction-terminated liquid mixture (liquid mixture before filtration)) was nearly 100%.

Molar Ratio in Flavonoid Inclusion Compound-Containing Composition (Rhamnose/Flavonoid)

In addition, the contents of rhamnose of the filtrates after the termination of the reaction of Examples 18 to 25, 27 to 31 and 101 to 109 were measured (a calibration curve was drawn with rhamnose (Wako) under the same conditions as the HPLC saccharide analysis), a molar concentration of rhamnose was then calculated. As a result, a molar ratio with flavonoid in an inclusion compound (rhamnose/flavonoid) was from 0.8 to 1.2.

Evaluations of Flavor of Flavonoid Inclusion Compound

One-hundred milliliters each of the reaction-terminated liquid mixtures of Examples 10 to 15 was placed into a dialysis membrane (Spectra/Por CE, dialysis tube, MWCO 500-1000, manufactured by funakoshi), dialysis was carried out in 10 L of water (exchanged five times with water at 10° C.) to remove rhamnose, and each liquid mixture was then lyophilized, to give 10 g to 30 g of dried products. The dried products obtained were added to a commercially available carbonated water (no sugar) ("Minami-Alps Tennensui, Sparkling," manufactured by Suntory), coffee beverage (no sugar) ("WONDA GOLD, BLACK," manufactured by Asahi Soft Drinks Co., Ltd.), and green tea ("Oi Ocha," manufactured by ITO EN, LTD.) in a concentration, which is a value calculated as 0.1% by mass in terms of isoquercitrin conversion, and sensory evaluations (off-flavor and sweetness) were made by five panelists using an additive-free product as a control. According to the following evaluation criteria, an average score of each was calculated. The results are shown in Table 3.

Evaluation Criteria of Off-Flavor
1: Strongly tasting off-flavor
2: Slightly strongly tasting off-flavor
3: Tasting off-flavor
4: Slightly tasting off-flavor
5: Not tasting off-flavor Evaluation Criteria of Sweetness
1: Strongly tasting sweetness
2: Slightly strongly tasting sweetness
3: Tasting sweetness
4: Slightly tasting sweetness
5: Not tasting sweetness citrin concentration: 2.3% by mass) to adjust its pH of 6.5 at 60° C. Thereafter, 20 g of cyclodextrin glucanotransferase (CGTase: Amano Enzyme Inc., trade name "Contizyme," 600 U/ml) was added thereto to initiate the reaction, and the reaction was maintained for 24 hours. The reaction liquid mixture obtained was thermally sterilized and filtered, and the reaction liquid mixture was lyophilized, to give 158 g of a composition of isoquercitrin glycosides containing a compound represented by general formula (1) (Sample 1). The solubility of the obtained composition of isoquercitrin glycosides (Sample 1) in water was a value calculated as 2.7%, in terms of isoquercitrin conversion. The obtained composition of isoquercitrin glycosides (Sample 1) was dissolved in water, the solution was then allowed to flow through a column packed with Diaion HP-20 (porous synthetic adsorption resin, manufactured by Mitsubishi Chemical Corporation), to allow the composition of isoquercitrin glycosides to be adsorbed to the column, and the column was washed with water in a volume two times that of the resin to remove saccharides such as rhamnose from the column. Thereafter, the eluted solution in which the adsorbed component was eluted with a 65% (v/v) ethanol in a volume two times that of the resin was concentrated, and the concentrated components were then lyophilized, to give a composition of glycosides of Example 39. The HPLC chromatogram of Example 39 is shown in FIG. 1. The results were the same as the HPLC chromatogram of Sample 1. In addition, the composition of isoquercitrin glycosides (Sample 1) was adsorbed and washed with water in the same manner as Example 39, and the composition was then eluted with ethanol at a concentration of from 10 to 60% (v/v). The

TABLE 3

|  | γCD/IQC | Carbonated Beverage | | Coffee Beverage | | Green Tea | |
| --- | --- | --- | --- | --- | --- | --- | --- |
|  | (molar ratio) | Off-Flavor | Sweetness | Off-Flavor | Sweetness | Off-Flavor | Sweetness |
| Ex. 10 | 1.0 | 4.1 | 4.0 | 4.0 | 3.9 | 4.1 | 4.0 |
| Ex. 11 | 1.5 | 4.0 | 3.9 | 3.8 | 3.7 | 4.0 | 4.0 |
| Ex. 12 | 1.8 | 3.7 | 3.6 | 3.8 | 3.7 | 3.5 | 3.4 |
| Ex. 13 | 2.0 | 1.3 | 2.6 | 1.3 | 2.5 | 1.4 | 2.7 |
| Ex. 14 | 3.0 | 1.3 | 2.2 | 1.2 | 2.3 | 1.3 | 2.4 |
| Ex. 15 | 4.0 | 1.1 | 1.9 | 1.1 | 2.1 | 1.1 | 1.9 |

As is clear from Table 3, it can be seen that when the products have molar ratios (γCD/IQC) of from 1.0 to 1.8, off-flavor and sweetness are lowered as compared to those having molar ratios of from 2.0 to 4.0, so that the products are preferred, from the viewpoint of reducing the effects to flavors of foods such as beverages. In addition, while not shown in the table, when as to a hesperetin-7-glucoside inclusion compound, when the molar ratio (CD/HPT-7G) is from 1.0 to 1.9, off-flavor (flavor different from the flavor of additive-free product) and sweetness are lowered as compared to those having molar ratios of from 2.0 to 3.0, so that the products can be suitably used in the foodstuff.

Preparation of Composition of Flavonoid Glycosides

Examples 32 to 39

A small amount of an alkali was added to reaction liquid mixture prepared in Example 4 (70° C., pH 4.5 and isoquersolutions in which a molar ratio was adjusted by combining those eluted solutions (10, 20, 30, 40, 50 and 60% (v/v) eluted solutions) were concentrated and then lyophilized, to give compositions of glycosides of Examples 32 to 38. The solubility of the compositions of glycosides of Examples 32 to 39 in water was a value calculated as 10% or more, in terms of isoquercitrin conversion. Here, at the time of the transglycosylation reaction, when reaction liquid mixtures at pHs of 7.5 and 8.5 were prepared with the same amount of enzyme, the compositions of isoquercitrin glycosides in nearly the same amounts were produced. However, the color of the solution turned dark brown due to a partial decomposition of the flavonoid, so that the composition reacted at a pH of 6.5 was used. Here, also in the reaction liquid mixtures prepared in Examples 1 to 3 and 10 to 16, compositions of isoquercitrin glycosides having the same HPLC chromatogram as Sample 1 (FIG. 1) were produced under the same conditions.

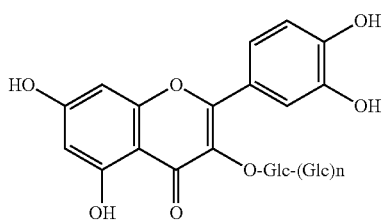

(1)

where in the general formula (1), Glc means a glucose residue, and n means an integer of 0 or 1 or more.

Examples 40 to 46

A small amount of an alkali was added to the reaction liquid mixture prepared in Example 22 (70° C., pH 4.5, hesperetin-7-glucoside concentration: 2.9% by mass) to adjust its pH of 6.5 at 60°. Thereafter, 5 g of cyclodextrin glucanotransferase (CGTase: Amano Enzyme Inc., trade name "Contizyme," 600 U/ml) was added thereto to initiate the reaction, and the reaction was maintained for 24 hours. The reaction liquid mixture obtained was thermally sterilized and filtered, and the reaction liquid mixture was then spray-dried, to give 136 g of a composition of glycosides of hesperetin-7-glucoside containing a compound represented by general formula (2) (Sample 2). The solubility of the obtained composition of glycosides of hesperetin-7-glucoside (Sample 2) in water was a value calculated as 5.1%, in terms of hesperetin-7-glucoside conversion. The composition of glycosides of hesperetin-7-glucoside obtained (Sample 2) was dissolved in water, the solution was then allowed to flow through a column packed with Diaion HP-20 (porous synthetic adsorption resin, manufactured by Mitsubishi Chemical Corporation), to allow the composition of glycosides of hesperetin-7-glucoside to be adsorbed to the column, and the column was washed with water in a volume two times that of the to remove the saccharides such as rhamnose from the column. Thereafter, the eluted solution in which the adsorbed component was eluted with a 65% (v/v) ethanol in volume two times that of the resin was concentrated, and the concentrated components were lyophilized, to give a composition of glycosides of Example 40. The HPLC chromatogram of Example 40 is shown in FIG. 2. The results were the same as the HPLC chromatogram of Sample 2. In addition, the composition of glycosides of hesperetin-7-glucoside (Sample 2) was adsorbed and washed with water in the same manner as Example 40, and the composition was then eluted with ethanol at a concentration of from 10 to 60% (v/v) which was used in elution. The solutions in which a molar ratio was adjusted by combining those eluted solutions (10, 20, 30, 40, 50 and 60% (v/v) of eluted solutions) were concentrated and then lyophilized, to give compositions of glycosides of Examples 41 to 46. The solubility of the compositions of glycosides of Examples 40 to 46 in water was a value calculated as 10% or more, in terms of hesperetin-7-glucoside conversion. Here, at the time of transglycosylation reaction, when reaction liquid mixtures at pHs of 7.5 and 8.5 were prepared with the same amount of enzyme, the compositions of glycosides of hesperetin-7-glucoside in the nearly same amounts were produced. However, the color of the solution turned dark brown due to a partial decomposition of the flavonoid, so that the composition reacted at a pH of 6.5 was used. Here, also in the reaction liquid mixtures prepared in Examples 21, 23 and 27 to 31, compositions of isoquercitrin glycosides having the same HPLC chromatogram as Sample 2 (FIG. 2) were produced under the same conditions.

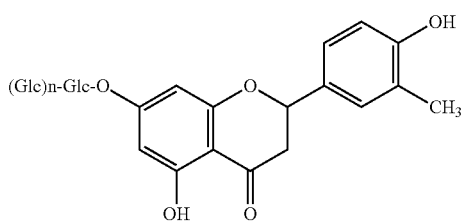

(2)

where in the general formula (2), Glc means a glucose residue, and n means an integer of 0 or 1 or more.

Solubility (Value Calculated as IQC, Value Calculated as HPT-7G)

The solubilities of Samples 1 and 2, and the compositions of flavonoid glycosides of Examples 32 to 46 were obtained by calculating an isoquercitrin concentration and a hesperetin-7-glucoside concentration according to the same methods as those of the solubility of IQC and the solubility of HPT-7G mentioned above to define a value calculated in terms of isoquercitrin conversion and a value calculated in terms of hesperetin-7-glucoside conversion. Here, compositions in which each value calculated was 10% or more and precipitates were not observed were described as compositions having solubility of 10% or more.

The molar ratios (%) in the compositions of flavonoid glycosides of Examples 32 to 46 were calculated in accordance with the following formula from the analytical results under the following conditions of HPLC (SIMADZU). The results are shown in Table 4. Here, each peak from n=0 to n=7 in FIGS. 1 and 2 was analyzed by LC/MS (liquid chromatography mass spectroscopy, SHIMADZU), to confirm the number of glycosides.

Molar Ratio (%)=Each Peak Area of Composition of Flavonoid Glycosides×100/Total Peak Area of Composition of Flavonoid Glycosides <Conditions of HPLC: Examples 32 to 39>
Column: CAPCELL PAK C18, SIZE 4.6 mm×250 mm (SHISEIDO)
Eluent: water/acetonitrile/phosphoric acid=799/200/1 (volume ratio)
Detection: Absorptiometric analysis at wavelength of 351 nm
Flow rate: 0.4 ml/min
Column temperature: 70° C.
<Conditions of HPLC: Examples 40 to 46
Column: CAPCELL PAK C18, SIZE 4.6 mm×250 mm (SHISEIDO)
Eluent: water/acetonitrile/phosphoric acid=849/150/1 (volume ratio)
Detection: Absorptiometric analysis at wavelength of 280 nm
Flow rate 0.4 ml/min
Column temperature: 70° C.

Evaluations of Flavors of Compositions of Flavonoid Glycosides

Lyophilized products of the compositions of flavonoid glycosides of Examples 32 to 46 were added to an acidic sugar solution (pH 3.1, Brix 10°) such that a concentration calculated terms of isoquercitrin was 0.05% (Examples 32 to 39) or a concentration calculated terms of hesperetin-7- glucoside was 0.05% (Examples 40 to 46). Sensory evaluations (bitterness, acridity and astringency) were made by seven panelists. According to the following evaluation criteria, each average score was calculated. Here, comparisons were made by defining evaluation scores for bitterness, acridity and astringency in a 0.05% isoquercitrin-containing acidic sugar solution prepared in Comparative Example 101 (solution immediately after preparation) as a strongest score of 1. In addition, since in the 0.05% isoquercitrin-containing acidic sugar solution, precipitates were not observed for 30 minutes at room temperature after the preparation, the sensory evaluations were carried out during that time. The results are shown in Table 4.

Evaluation Criteria of Bitterness
1: Strongly tasting bitterness
2: Slightly strongly tasting bitterness
3: Tasting bitterness
4: Slightly tasting bitterness
5: Not tasting bitterness Evaluation Criteria of Acridity
1: Strongly tasting acridity
2: Slightly strongly tasting acridity
3: Tasting acridity
4: Slightly tasting acridity
5: Not tasting acridity Evaluation Criteria of Astringency
1: Strongly tasting astringency
2: Slightly strongly tasting astringency
3: Feel astringency
4: Slightly tasting astringency
5: Not tasting astringency As is clear from Table 4, the compositions of glycosides of Examples 36, 38, 39, 40 and 41 in which the content of glycosides having $n=0$ is 10% by mol or more and 30% by mol or less, the content of glycosides having $n=1$ to 3 is 50% by mol or less, and the content of glycosides having $n=4$ or more is 30% by mol or more in general formulas (1) and (2) have significantly lowered bitterness, acridity and astringency in the sensory evaluations with acidic sugar solutions, so that the compositions can be suitably used in the applications of foodstuff. Here, since all the compositions of glycosides of Examples 32 to 46 have excellent solubilities, these compositions can be suitably used in applications irrelevant of flavors, for example, applications of cosmetics and the like. In addition, although not shown in tables, as to the compositions of glycosides of naringenin-7-glucoside obtained by using the reaction liquid mixtures prepared in Examples 104 to 106, bitterness, acridity and astringency were significantly lowered in accordance with the sensory evaluations by a concentration of a value calculated as 0.05% in terms of naringenin-7-glucoside conversion in an acidic sugar solution when the content of glycosides having $n=0$ is 10% by mol or more and 30% by mol or less, the content of glycosides having $n=1$ to 3 is 50% by mol or less, and the content of glycosides having $n=4$ or more is 30% by mol or more.

Molar Ratio in Compositions of Flavonoid Glycosides (Rhamnose/Flavonoid)

The molar ratio of a molar concentration calculated after the measurements of the rhamnose content of Samples 1 and 2 (a calibration curve was drawn with rhamnose (WAKO) under the same conditions as HPLC saccharide analysis), to a molar concentration calculated from a value calculated in

TABLE 4

| | Numerical Figures of n in General Formulas (1) and (2) (Molar Ratio (%)) | | | | | | | | | | |
|---|---|---|---|---|---|---|---|---|---|---|---|
| | 0 | 1 | 2 | 3 | 4 | 5 | 6 | 7 or more | Bitterness | Acridity | Astringency |
| Ex. 32 | 47.3 | 14.4 | 10.6 | 7.8 | 5.6 | 7.3 | 6.0 | 1.0 | 1.5 | 1.2 | 1.5 |
| | 47.3 | | 32.8 | | | 19.9 | | | | | |
| Ex. 33 | 9.0 | 27.7 | 23.2 | 20.1 | 6.8 | 5.2 | 8.0 | 0.0 | 1.8 | 1.8 | 1.9 |
| | 9.0 | | 71.0 | | | 20.0 | | | | | |
| Ex. 34 | 31.0 | 23.6 | 22.1 | 10.1 | 5.9 | 5.9 | 0.9 | 0.5 | 1.9 | 1.6 | 2.0 |
| | 31.0 | | 55.8 | | | 13.2 | | | | | |
| Ex. 35 | 22.0 | 21.0 | 23.0 | 13.0 | 8.5 | 5.0 | 3.1 | 4.4 | 1.9 | 2.5 | 1.8 |
| | 22.0 | | 57.0 | | | 21.0 | | | | | |
| Ex. 36 | 27.0 | 18.0 | 13.0 | 7.0 | 12.7 | 13.2 | 4.9 | 4.2 | 4.2 | 4.1 | 3.9 |
| | 27.0 | | 38.0 | | | 35.0 | | | | | |
| Ex. 37 | 18.2 | 20.0 | 18.0 | 18.0. | 8.1 | 6.9 | 6.7 | 4.1 | 2.0 | 2.1 | 2.2 |
| | 18.2 | | 56.0 | | | 25.8 | | | | | |
| Ex. 38 | 20.9 | 14.7 | 12.8 | 11.1 | 8.8 | 7.3 | 6.1 | 18.2 | 4.8 | 4.5 | 3.9 |
| | 20.9 | | 38.5 | | | 40.6 | | | | | |
| Ex. 39 | 16.2 | 14.7 | 13.9 | 12.1 | 9.1 | 7.9 | 6.7 | 19.3 | 4.0 | 4.9 | 4.8 |
| | 16.2 | | 40.7 | | | 43.1 | | | | | |
| Ex. 40 | 19.5 | 16.2 | 13.8 | 10.9 | 9.5 | 7.0 | 5.5 | 17.6 | 4.1 | 4.0 | 4.1 |
| | 19.5 | | 40.9 | | | 39.6 | | | | | |
| Ex. 41 | 15.1 | 17.3 | 16.3 | 12.7 | 8.4 | 7.0 | 5.0 | 18.2 | 4.2 | 4.3 | 4.2 |
| | 15.1 | | 46.3 | | | 38.6 | | | | | |
| Ex. 42 | 8.0 | 25.0 | 20.0 | 14.8 | 7.5 | 5.9 | 4.7 | 14.1 | 2.3 | 2.5 | 2.5 |
| | 8.0 | | 59.8 | | | 32.2 | | | | | |
| Ex. 43 | 22.0 | 20.6 | 17.0 | 16.5 | 7.0 | 5.5 | 5.0 | 6.4 | 1.9 | 2.0 | 2.1 |
| | 22.0 | | 54.1 | | | 23.9 | | | | | |
| Ex. 44 | 35.0 | 21.3 | 18.1 | 12.6 | 4.3 | 3.0 | 2.7 | 3.0 | 1.9 | 2.1 | 1.8 |
| | 35.0 | | 52.0 | | | 13.0 | | | | | |
| Ex. 45 | 46.7 | 17.2 | 9.3 | 4.6 | 5.0 | 4.1 | 4.8 | 8.3 | 1.2 | 1.3 | 1.5 |
| | 46.7 | | 31.1 | | | 22.2 | | | | | |
| Ex. 46 | 13.4 | 29.8 | 28.2 | 16.7 | 2.2 | 1.5 | 2.2 | 6.0 | 1.8 | 1.9 | 1.8 |
| | 13.4 | | 74.7 | | | 11.9 | | | | | | terms of isoquercitrin conversion and a value calculated in terms of hesperetin-7-glucoside conversion (rhamnose/flavonoid) was from 0.8 to 1.2.

Evaluations of Fading-Preventing Effects

A flavonoid inclusion compound-containing composition of Example 16 and a composition of flavonoid glycosides of Example 39 were added to a 0.05% red cabbage color formulation-containing acidic sugar solution (pH 3.0) so as to have a concentration of 0.005% calculated in terms of isoquercitrin conversion. The mixture was subjected to a ultraviolet fade meter treatment for 4 hours, and thereafter a color-residual percent was compared. As a result, the fading-preventing effects were observed as compared to an additive-free product. The results are shown in Table 5.

TABLE 5

|  | Color-Residual Percent (%) |
| --- | --- |
| Example 16 | 96 |
| Example 39 | 95 |
| Additive-free Product | 56 |

As is clear from Table 5, the fading-preventing effects against red cabbage color were observed in the isoquercitrin-γ-cyclodextrin inclusion compound-containing composition and the composition of isoquercitrin glycosides.

Evaluations of Effects of Preventing Flavor Deterioration (Milk)

One-hundred milliliters of a reaction-terminated liquid mixture of Example 16 was placed into a dialysis membrane (Spectra/Por CE, dialysis tube, MWCO 500-1000, manufactured by funakoshi), dialysis was carried out in 10 L of water (exchanged five times with water at 10° C.) to remove rhamnose, and the solution was lyophilized to give 22 g of dried products. The dried products obtained and the composition of flavonoid glycosides of Example 39 were added to a commercially available milk (3.5% milk fat, "Meiji Nyugyo," manufactured by Meiji Co., Ltd.) so as to have a concentration of a value calculated as 0.005% in terms of isoquercitrin conversion in a 100 ml transparent glass bottle. The flavors after fluorescent lamp illumination (20,000 1×, 5 hours, 10° C.) were compared as an average score of ten panelists according to the following evaluation criteria. As a result, the effects for preventing flavor deterioration were observed. The results are shown in Table 6.

<Evaluation Criteria>
1: Markedly changed from unilluminated product
2: Considerably changed from unilluminated product
3: Somewhat changed from unilluminated product
4: Very slightly changed from unilluminated product
5: Not changed from unilluminated product

TABLE 6

|  | Effects of Preventing Flavor Deterioration (Milk) |
| --- | --- |
| Example 16 | 3.8 |
| Example 39 | 3.9 |
| Additive-free Product | 2.2 |

As is clear from Table 6, the effects of preventing flavor deterioration were observed in milk with an isoquercitrin-γ-cyclodextrin inclusion compound and a composition of isoquercitrin glycosides.

Evaluations of Effects of Preventing Flavor Deterioration (Jelly)

Grapefruit jelly, an additive-free product, was prepared by using 0.5% of grapefruit fruit juice (⅕), 3% of gelatin, 1% of grapefruit juice sac, 6% of maltitol, and 0.025% of safflower yellow color formulation as raw materials. One-hundred milliliters of the reaction-terminated liquid mixture of Example 22 or 28 was placed into a dialysis membrane (Spectra/Por CE, dialysis tube, MWCO 500-1000, manufactured by funakoshi), dialysis was carried out in 10 L of water (exchanged five times with water at 10° C.) to remove rhamnose, and the solution was lyophilized to give 12 g of dried products from Example 22 and 16 g of dried products from Example 28. Each of the dried products obtained and the composition of flavonoid glycosides of Example 40 were added to the grapefruit jelly, the additive-free product, so as to have a concentration of a value calculated as 0.005% in terms of hesperetin-7-glucoside conversion to give a grapefruit jelly which is an additive-including product, respectively. Thereafter, the jelly was heated to 93° C., the heated product was filled into a transparent glass bottle and these contents were tightly sealed in the bottle, and the bottle was then cooled and stored for one month in a room which was illuminated with normal fluorescent lamp at room temperature. Thereafter, the flavor was compared in average scores by ten panelists according to the following evaluation criteria. As a result, the effects of preventing flavor deterioration were observed in each additive-including product. The results are shown in Table 7.

<Evaluation Criteria>
1: Markedly changed from unilluminated product
2: Considerably changed from unilluminated product
3: Somewhat changed from unilluminated product
4: Slightly changed from unilluminated product
5: Unchanged from unilluminated product

TABLE 7

|  | Effects of Preventing Flavor Deterioration (Jelly) |
| --- | --- |
| Example 22 | 4.1 |
| Example 28 | 4.0 |
| Example 40 | 4.2 |
| Additive-free Product | 1.9 |

As is clear from Table 7, the effects of preventing flavor deterioration in grapefruit jelly were observed by a hesperetin-7-glucoside-β-cyclodextrin inclusion compound, a hesperetin-7-glucoside-γ-cyclodextrin inclusion compound and a composition of glycosides of hesperetin-7-glucoside.

Evaluation of Storage Stability (Acidic Sugar Solution)

The isoquercitrin prepared in Comparative Example 101, the flavonoid inclusion compound-containing composition of Example 16 and the composition of flavonoid glycosides of Example 39 were dissolved in an acidic sugar solution having a pH of 3 composed of the following compositions so as to have a concentration calculated as 0.03% in terms of isoquercitrin conversion, and the solution was subjected to hot-pack filling into a 100 ml glass bottle (93° C.). After air-cooling, the prepared solutions were allowed to stand for 4 months under the conditions of 4° C., 25° C. and 40° C., respectively, and the presence or absence of the precipitates was visually observed. Those solutions that were transparent in which the precipitates were not observed were evaluated as ◯ and those in which the precipitates were observed were evaluated as X. The results are shown in Table 8.

Composition of Acidic Sugar Solution

|  | (% by mass) |
| --- | --- |
| 1. Sugar | 10 |
| 2. (Crystalline) Citric Acid | 0.08 |
| 3. Trisodium Citrate | pH adjusted (pH 3) |
| 4. Water | Balance |

TABLE 8

|  | 4° C. | 25° C. | 40° C. |
| --- | --- | --- | --- |
| Isoquercitrin | X | X | X |
| Example 16 | ○ | ○ | ○ |
| Example 39 | ○ | ○ | ○ |

As shown in Table 8, when isoquercitrin was added to the acidic sugar solution, the precipitates were observed immediately after storages at all of the refrigeration (4° C.), room temperature (25° C.) and 40° C. However, in the case where the isoquercitrin-γ-cyclodextrin inclusion compound and the composition of isoquercitrin glycosides were added, the precipitates were not observed even when the solutions were allowed to stand for 4 months, and further the precipitates were not observed even in a long-term storage of 5 months.

Evaluation of Storage Stability (Green Tea)

Hesperidin (manufactured by Hamari Chemicals., Ltd.), hesperetin-7-glucoside (prepared in the following), a flavonoid inclusion compound of Example 22 or a composition of flavonoid glycosides of Example 40 was added to a commercially available green tea ("Oi Ocha," manufactured by ITO EN, LTD.) so as to have a concentration calculated as 0.03% in terms of hesperetin-7-glucoside conversion. The mixture was allowed to stand for 7 days at 4° C. and 25° C., and the presence or absence of the precipitates was then visually observed. Those solutions that were transparent in which the precipitates were not observed were evaluated as ○, and those in which the precipitates were observed were evaluated as x. The results are shown in Table 9.

Seven grams of Hesperidin (manufactured by Hamari Chemicals., Ltd.) was added to 100 L of an aqueous solution, and the solution was adjusted to 70° C. and a pH of 4.5. Thereafter, 0.5 g of naringinase (Amano Enzyme Inc. 155 u/g) was added thereto while stirring, and the solution was recovered and dried, to give 4.2 g of hesperetin-7-glucoside having a content of 96% or more. Identification as being hesperetin-7-glucoside and a content thereof were analyzed by NMR and HPLC in the same manner as mentioned above.

TABLE 9

|  | 4° C. | 25° C. |
| --- | --- | --- |
| Hesperidin | X | X |
| Hesperetin-7-Glucoside | X | X |
| Example 22 | ○ | ○ |
| Example 40 | ○ | ○ |

As shown in Table 9, when hesperidin or hesperetin-7-glucoside was added to a green tea, the precipitates were observed immediately after storages at both refrigeration (4° C.) and room temperature (25° C.). However, in the case where the hesperetin-7-glucoside inclusion compound-containing composition and the composition of glycosides of hesperetin-7-glucoside were added, the precipitates were not observed even when the green tea was allowed to stand for 7 days.

Evaluation of Storage Stability (Lemon Beverage)

Naringin (manufactured by SIGMA), naringenin-7-glucoside (prepared hereinbelow) or a flavonoid inclusion compound-containing composition of Example 109 was added to a commercially available lemon beverage (C1000 Lemon Water, manufactured by HOUSE WELLNESS FOODS CORPORATION) so as to have a concentration calculated as 0.3% in terms of naringenin-7-glucoside conversion, the beverage was allowed to stand for 1 month at 4° C. or 25° C., and the presence or absence of the precipitates was then visually observed. Those solutions that were transparent in which the precipitates were not observed were evaluated as ○ and those in which the precipitates were observed were evaluated as x. The results are shown in Table 9-2.

After the termination of the reaction according to Comparative Example 102, the precipitates that were previously allowed to stand at room temperature were recovered, washed with water, recrystallized and dried, to give 13 g of naringenin-7-glucoside having a content of 95% or more. The identity of the product with a reagent naringenin-7-glucoside (Wako) by HPLC and a content thereof were analyzed.

TABLE 9-2

|  | 4° C. | 25° C. |
| --- | --- | --- |
| Naringin | X | X |
| Naringenin-7-glucoside | X | X |
| Example 109 | ○ | ○ |

As shown in Table 9-2, when naringin or naringenin-7-glucoside was added to a lemon beverage, the precipitates were observed in both the storages at refrigeration (4° C.) and room temperature (25° C.). However, in a case where the naringenin-7-glucoside inclusion compound-containing composition was added, the precipitates were not observed even when the beverage was allowed to stand for 1 month.

Evaluation of Bioavailability

Nine-week-old Wister rats (male) were given with MF (Oriental Yeast Co., Ltd.) and bred for 7 days, and the rats were then subjected to fasting from the day before the administration of a test substance. Thereafter, 100 μmol/kg (calculated as IQC) of a dried product of Example 16 prepared in the evaluation of the effects of preventing flavor deterioration, a rutin suspension (Alps Pharmaceutical Ind., Co., Ltd., 100 μmol/kg (calculated as IQC)), 1,000 μmol/kg (calculated as HPT-7G) of dried product of Example 22 prepared in the evaluations of the effects of preventing flavor deterioration, and a hesperidin suspension (Hamari Chemicals., Ltd., 1,000 μmol/kg (calculated as HPT-7G)) were orally administered to the rats in a single dose (orally administered by gavage, n=2). Blood collection into heparinized tubes was carried out from tail veins of rats 30 minutes, 1 hour and 3 hours after the administration, and the blood was centrifuged to obtain plasma. In the drawn sera sample, the amounts of quercetin derivatives were measured according to a method by Makino et al (*Biol. pharm. Bull.*, 32(12) 2034, 2009), and the amounts of hesperetin derivatives were measured according to a method by Yamada et al (*Biosci. Biotechnol. Biochem*, 70(6), 1386, 2006), and analysis was made by applying the sample to high-performance liquid chromatography (SHIMADZU) and using a photodiode array detector (SPD-M30A, SHIMADZU). The results are shown in Tables 10 and 11. Table 10 showed the concentrations of quercetin and quercetin derivatives (isorhamnetin, tamarixetin) (µM) at the time of from 0 to 3 hours, and the area under the blood concentration-time curve (AUC) of a total amount thereof (µM·h). In addition, since the hesperetin derivative was not detected, Table 11 showed a concentration of hesperetin (µM) at the time of from 0 to 3 hours, and the area under the curve (AUC) of the blood concentration-time thereof (µM·h).

TABLE 10

|  | Time of Blood Drawing | Rutin Suspension | Example 16 |
|---|---|---|---|
| Quercetin (µM) | 0 | 0 | 0 |
|  | 0.5 | 0 | 9.3 |
|  | 1 | 0.004 | 10.3 |
|  | 3 | 0 | 6.9 |
| Isorhamnetin (µM) | 0 | 0 | 0 |
|  | 0.5 | 0 | 0.3 |
|  | 1 | 0.004 | 0.3 |
|  | 3 | 0 | 0.2 |
| Tamarixetin (µM) |  | 0 | 0 |
|  | 0.5 | 0 | 2.1 |
|  | 1 | 0.01 | 3.6 |
|  | 3 | 0.08 | 4.2 |
| Total (µM) | 0 | 0 | 0 |
|  | 0.5 | 0 | 11.6 |
|  | 1 | 0.018 | 14.2 |
|  | 3 | 0.08 | 11.3 |
| AUC (µM · h) | Total | 0.1 | 34.9 |

TABLE 11

|  | Time of Blood Drawing | Hesperidin Suspension | Example 22 |
|---|---|---|---|
| Hesperetin (µM) | 0 | 0 | 0 |
|  | 0.5 | 0.003 | 113.5 |
|  | 1 | 0.064 | 130.2 |
|  | 3 | 0 | 52.6 |
| AUC(µM · h) | Total | 0.082 | 272.0 |

As shown in Tables 10 and 11, it could be seen in the comparison of AUC of from 0 to 3 hours that the isoquercitrin-γ-cyclodextrin inclusion compound or the hesperetin-7-glucoside-β-cyclodextrin inclusion compound was efficiently absorbed by rats, as compared to rutin or hesperidin. In addition, while not shown in Tables, the bioavailability of 100 µmol/kg (calculated as IQC) of the composition of isoquercitrin glycosides of Example 39 was nearly the same as that of Example 16, and the bioavailability of 1,000 µmol/kg (calculated as HPT-7G) of the composition of glycosides of hesperetin-7-glucoside of Example 40 was nearly the same as that of Example 22.

Solubility Improving Effects of Sparingly Soluble Flavonoid

Examples 110 to 113

An inclusion compound of rutin (RTN) and isoquercitrin with γ-cyclodextrin (IQC-rCD) was dissolved in an acidic sugar solution (pH 3.1, Brix 10°) in amounts of the components as listed in Table 12, and the solution was subjected to a hot-pack filling into a 100 ml glass bottle. The prepared solution was air-cooled and subjected to refrigeration storage (4° C., 6 months), and the presence or absence of the precipitates was then visually observed. The results are shown in Table 12.

Comparative Examples 103 to 106, and Referential Example

The same procedures as in Examples 110 to 113 were carried out in preparation, air-cooling and refrigeration storage, except that rutin (RTN) and isoquercitrin (IQC) were dissolved in an acidic sugar solution in amounts of the components as listed in Table 13, and the presence or absence of the precipitates was visually observed. The results are shown in Table 13.

In Tables 12 and 13, IQC/RTN (molar ratio) was obtained by analyzing HPLC (SHIMADZU, the same conditions as those of conversion rate) using 1 ml of an acidic sugar solution immediately after dissolving the preparation components as a measurement sample, and then expressing an areal ratio (peak area of isoquercitrin/peak area of rutin) as a molar ratio.

TABLE 12

|  | (41) RTN (% by mass) | (42) IQC-γCD (% by mass) | (43) IQC (% by mass) | (44) γCD (% by mass) | (45) Solubility | (46) IQC/RTN (molar ratio) |
|---|---|---|---|---|---|---|
| Ex. 110 | 0.05 | 0.02 | 0.005 | 0.014 | − | 0.13 |
| Ex. 111 | 0.05 | 0.04 | 0.01 | 0.028 | − | 0.26 |
| Ex. 112 | 0.05 | 0.08 | 0.02 | 0.056 | − | 0.53 |
| Ex. 113 | 0.05 | 0.09 | 0.025 | 0.070 | − | 0.66 |

TABLE 13

|  | (41) RTN (% by mass) | (42) IQC-γCD (% by mass) | (43) IQC (% by mass) | (44) γCD (% by mass) | (45) Solubility | (46) IQC/RTN (molar ratio) |
|---|---|---|---|---|---|---|
| Comp. Ex. 103 | 0.05 | 0 | 0.005 | 0 | ++ | 0.13 |
| Comp. Ex. 104 | 0.05 | 0 | 0.01 | 0 | ++ | 0.26 |
| Comp. Ex. 105 | 0.05 | 0 | 0.02 | 0 | ++ | 0.53 |
| Comp. Ex. 106 | 0.05 | 0 | 0.025 | 0 | ++ | 0.66 |
| Ref. Ex. | 0.05 | 0 | 0 | 0 | +++ | 0.003 |

Notes of Tables 12 and 13
(41) Rutin concentration in an acidic sugar solution (% by mass)
(42) Isoquercitrin-γ-cyclodextrin inclusion compound concentration in an acidic sugar solution (% by mass)
(43) Isoquercitrin concentration in an acidic sugar solution (% by mass)
(44) γ-Cyclodextrin concentration in an acidic sugar solution (% by mass)
(45) Solubility:
The precipitates were not observed: −
The amount of the precipitates was small: +
The amount of the precipitates was sligh0tly large: ++
The amount of the precipitates was large: +++
(46) Isoquercitrin/rutin in an acidic sugar solution (molar ratio)

As shown in Tables 12 and 13, in Examples 110 to 113 in which the isoquercitrin-γ-cyclodextrin inclusion compound was added, the solubility of rutin was improved, and the precipitates were not observed especially when the molar ratio of isoquercitrin and rutin (isoquercitrin/rutin) was within a range of from 0.1 to 0.7. The same results as these were also shown in the lyophilized products of the flavonoid inclusion compounds of Examples 10, 13 and 14 (products in which rhamnose was removed by dialysis) and the lyophilized product of the flavonoid inclusion compound-containing composition containing rhamnose. On the other hand, as shown in Table 13, in the products in which with only isoquercitrin was added, the precipitates were observed in all cases.

In addition, in Tables 12 and 13, the same results were also obtained in isoquercitrin and isoquercitrin-β-cyclodextrin (lyophilized products of Examples 1 to 7), or hesperidin and hesperetin-7-glucoside-β-cyclodextrin (lyophilized products of Examples 18 to 23) in place of rutin, or hesperetin-7-glucoside-γ-cyclodextrin (lyophilized products of Examples 27 to 31).

Evaluation of Long-Term Stability and Astringency of Isoquercitrin-γ-Cyclodextrin Inclusion Compound Examples 114 to 117

Solutions were prepared in the same manner as Examples 110 to 113 except that the amounts of components as listed in Table 14 were used. Immediately after air-cooling, sensory evaluations for astringency were carried out therewith. In addition, solutions having the same amounts of components were separately prepared, and subjected to refrigeration storage (4° C., 12 months), and the presence or absence of the precipitates was then visually observed. The results are shown in Table 14.

Comparative Examples 107 to 110

Solutions were prepared in the same manner as Examples 103 to 106 except that the amounts of components listed in Table 15 were used. Immediately after air-cooling, sensory evaluations for astringency was carried out therewith. In addition, solutions having the same amounts of components were separately prepared, the solutions were stored at refrigeration (4° C., 12 months). Thereafter, the presence or absence of the precipitates was visually observed. The results are shown in Table 15.

In Tables 14 and 15, RTN/IQC (molar ratio) was obtained by analyzing HPLC (SHIMADZU, the same conditions as those of conversion rate) using 1 ml of an acidic sugar solution immediately after dissolving the preparation components as a measurement sample, and then expressing an areal ratio (peak area of rutin/peak area of isoquercitrin) as a molar ratio.

TABLE 14

| | (51) IQC-γCD (% by mass) | (52) IQC (% by mass) | (53) γCD (% by mass) | (54) RTN (% by mass) | (55) Solubility | (56) RTN/IQC (molar ratio) | (57) Astringency |
|---|---|---|---|---|---|---|---|
| Ex. 114 | 0.38 | 0.1 | 0.28 | 0.0004 | − | 0.003 | 1.2 |
| Ex. 115 | 0.38 | 0.1 | 0.28 | 0.001 | − | 0.01 | 1.3 |
| Ex. 116 | 0.38 | 0.1 | 0.28 | 0.005 | − | 0.04 | 1.3 |
| Ex. 117 | 0.38 | 0.1 | 0.28 | 0.01 | − | 0.08 | 1.3 |

TABLE 15

| | (51) IQC-γCD (% by mass) | (52) IQC (% by mass) | (53) γCD (% by mass) | (54) RTN (% by mass) | (55) Solubility | (56) RTN/IQC (molar ratio) | (57) Astringency |
|---|---|---|---|---|---|---|---|
| Comp. Ex. 107 | 0 | 0.1 | 0 | 0.0004 | +++ | 0.003 | 2.7 |
| Comp. Ex. 108 | 0 | 0.1 | 0 | 0.001 | ++ | 0.01 | 2.8 |
| Comp. Ex. 109 | 0 | 0.1 | 0 | 0.005 | ++ | 0.04 | 2.8 |
| Comp. Ex. 110 | 0 | 0.1 | 0 | 0.01 | ++ | 0.08 | 3.0 |

Notes of Tables 14 and 15
(51) Isoquercitrin-γ-cyclodextrin inclusion compound concentration in an acidic sugar solution (% by mass)
(52) Isoquercitrin concentration in an acidic sugar solution (% by mass)
(53) γ-Cyclodextrin concentration in an acidic sugar solution (% by mass)
(54) Rutin concentration in an acidic sugar solution (% by mass)
(55) Solubility:
The precipitates were not observed: −
The amount of the precipitates was small: +
The amount of the precipitates was slightly large: ++
The amount of the precipitates was large: +++
(56) Rutin/isoquercitrin in an acidic sugar solution (molar ratio)
(57) Immediately after preparation and air-cooling of an acidic sugar solution, ten panelists scored a sample in which astringency was most strongly tasted as compared to the additive-free acidic sugar solution as 3 points, and followed by 2 points and 1 point, and an average thereof was shown.

Here, since the precipitates were not observed after the preparation and air-cooling of Comparative Examples 107 to 110 for 30 minutes at room temperature, sensory evaluations were carried out during that time.

As shown in Table 14, it was confirmed that even when rutin was contained in a specified amount in a composition containing an inclusion compound of isoquercitrin and γ-cyclodextrin obtained in the production method of the present invention, there were no disadvantages in long-term stability of the inclusion compound. In addition, it was confirmed that astringency would be weak, so that influences on flavors when added to foodstuff were small. When the RTN/IQC (molar ratio) was within a range of 0.08 or less (Examples 114 to 117), astringency was particularly weak. The same results are also shown in the lyophilized products of flavonoid inclusion compounds of Examples 10, 13 and 14 (in which rhamnose was removed by dialysis) and the lyophilized products of a flavonoid inclusion compound-containing composition containing rhamnose. On the other hand, as shown in Table 15, in a composition containing isoquercitrin, when the composition contained rutin, the precipitates were observed in all the compositions, and astringency was also strong.

Also, in Tables 14 and 15, the same results were also obtained in isoquercitrin and isoquercitrin-β-cyclodextrin (lyophilized products of Examples 1 to 7), hesperidin and hesperetin-7-glucoside-β-cyclodextrin (lyophilized products of Examples 18 to 23) in place of rutin, or hesperetin-7-glucoside-γ-cyclodextrin (lyophilized products of Examples 27 to 31).

The details of the components used in Examples 110 to 117, Comparative Examples 103 to 110, and Referential Example are shown hereinbelow.

RTN: Heat dissolved product of 90 g of 99.5% by volume ethanol and 10 g of rutin (preparation product: molar ratio of isoquercitrin/rutin being 0.3/99.7)

IQC-rCD: Lyophilized product of Example 16 (product in which rhamnose was removed by dialysis (molar ratio of rutin/isoquercitrin being 0.3/99.7))

IQC: Thermally dissolved product of 18 g of 99.5% by volume ethanol and 2 g of isoquercitrin (preparation product: molar ratio of rutin/isoquercitrin being 0.3/99.7)

Formulation Examples of Flavonoid Inclusion Compound-Containing Composition and Composition of Flavonoid Glycosides

Formulation Example 1

Grapefruit Beverage

For the purpose of preventing flavor deterioration, beverage containing a dried product of an isoquercitrin-γ-cyclodextrin inclusion compound-containing composition of Example 16 was prepared. The present product can be suitably utilized as beverage.

| Component | % by mass |
| --- | --- |
| Concentrated Grapefruit Juice | 5.0 |
| Glucose-Fructose Syrup | 0.9 |
| Maltitol | 2.0 |
| Acidulant | 0.3 |
| Vitamin C | 0.02 |
| Flavor | 0.1 |
| Dried Product of Example 16 | 0.02 |
| Water | Balance |
| Total | 100 |

Formulation Example 2

Jelly

For the purpose of preventing flavor deterioration, a jelly containing a dried product of a hesperetin-7-glucoside-β-cyclodextrin inclusion compound-containing composition of Example 22 was prepared. The present product can be suitably utilized as a food (jelly).

| Component | % by mass |
| --- | --- |
| Sugar | 10.0 |
| Concentrated Lemon Juice | 8.5 |
| *Gardenia* Yellow Preparation | 0.004 |
| Acidulant | 1.0 |
| Gelating Agent | 1.5 |
| Vitamin C | 0.02 |
| Flavors | 0.2 |
| Dried Product of Example 22 | 0.04 |
| Water | Balance |
| Total | 100 |

Formulation Example 3

Cosmetics

For the purpose of skin improvement in dullness and edema-related swelling, cosmetics containing a dried product of a composition of glycosides of hesperetin-7-glucoside of Example 40 were prepared. The present product can be suitably utilized as skincare cosmetics.

| Component | % by mass |
| --- | --- |
| Glycerol | 5.0 |
| Propylene Glycol | 4.0 |
| Oleyl Alcohol | 0.1 |
| Surfactant | 2.0 |
| Ethyl Alcohol | 10.0 |
| Perfume | 0.1 |
| Dried Product of Example 40 | 0.26 |
| Purified Water | Balance |
| Total | 100 |

Formulation Example 4

Tablet

For the purpose of moderating body temperature, a tablet containing a dried product of a hesperetin-7-glucoside-β-cyclodextrin inclusion compound-containing composition of Example 22 was prepared. The present product can be suitably utilized as health foods.

| Component | % by mass |
| --- | --- |
| Maltitol | 69.0 |
| Trehalose | 12.9 |
| Acidulant | 2.5 |
| Calcium Stearate | 0.5 |
| Vitamin C | 0.02 |
| Flavors | 0.08 |
| Dried Product of Example 22 | 15.0 |
| Total | 100 |

Formulation Example 5

Coffee Beverage

For the purpose of reducing body fat, a coffee beverage containing a dried product of a composition of isoquercitrin glycosides of Example 39 was prepared. The present product can be suitably utilized as foods for specified health use.

| Component | % by mass |
| --- | --- |
| Coffee Extract | 32.6 |
| Sugar | 6.0 |
| Flavors | 0.06 |
| Dried Product of Example 39 | 0.06 |
| Water | Balance |
| Total | 100 |

Formulation Example 6

Black Tea Beverage

For the purpose of reducing neutral fat, a black tea beverage containing a dried product of a composition of glycosides of hesperetin-7-glucoside of Example 40 was prepared. The present product can be suitably utilized as foods with function claims.

| Component | % by mass |
| --- | --- |
| Black Tea Extract | 18.6 |
| Sodium Hydrogencarbonate | 0.002 |
| Sucralose | 0.003 |
| Vitamin C | 0.03 |
| Flavors | 0.1 |
| Dried Product of Example 40 | 0.06 |
| Water | Balance |
| Total | 100 |

Formulation Example 7

Hair Restorer

For the purpose of improving scalp, a hair restorer containing a dried product of a hesperetin-7-glucoside-β-cyclodextrin inclusion compound-containing composition of Example 22 was prepared.

| Component | % by mass |
| --- | --- |
| Ethyl Alcohol | 60.0 |
| *Swertia japonica* Extract | 5.0 |
| Tocopherol Acetate | 0.2 |
| Panthenyl Ethyl Ether | 0.2 |
| Propylene Glycol | 5.0 |
| Preservative | 0.1 |
| Perfume | 0.2 |
| Dried Product of Example 22 | 0.03 |
| Purified Water | Balance |
| Total | 100 |

Formulation Example 8

Hair Shampoo

For the purpose of preventing inflammation, a hair shampoo containing a dried product of a hesperetin-7-glucoside-γ-cyclodextrin inclusion compound-containing composition of Example 27 was prepared.

| Component | % by mass |
| --- | --- |
| Sodium Polyoxyethylene(2) Lauryl Ether Sulfate | 9.0 |
| Sodium Lauryl Sulfate | 4.0 |
| Cocamidopropyl Betaine | 3.0 |
| High Polymerized Methyl Polysiloxane | 2.0 |
| Methyl Polysiloxane | 1.0 |
| Coconut Oil Fatty Acid Monoethanolamide | 1.0 |
| Propylene Glycol | 2.0 |
| Ethylene Glycol Distearate | 2.0 |
| Preservative | 0.1 |
| Perfume | 0.1 |
| Dried Product of Example 27 | 0.03 |
| Water | Balance |
| Total | 100 |

Formulation Example 9

Tablet for Diet

For the purpose of a diet, a tablet containing a dried product of a naringenin-7-glucoside-β-cyclodextrin inclusion compound-containing composition of Example 109 was prepared. The present product can be suitably utilized as health foods.

| Component | % by mass |
| --- | --- |
| Maltitol | 64.0 |
| Trehalose | 12.9 |
| Acidulant | 2.5 |
| Calcium Stearate | 0.5 |
| Vitamin C | 0.02 |
| Flavors | 0.08 |
| Dried Product of Example 109 | 20.0 |
| Total | 100 |

INDUSTRIAL APPLICABILITY

According to the production method of the present invention, a flavonoid inclusion compound and a composition of flavonoid glycosides having excellent solubility in water can be efficiently produced, so that the compound and composition can be suitably utilized in the fields of medicament, foodstuff, health foods, foods for specified health use, cosmetics, and the like.

The invention claimed is:

1. A flavonoid inclusion compound-containing composition comprising a flavonoid inclusion compound and a rhamnose, wherein a molar ratio of a flavonoid in the flavonoid inclusion compound and the rhamnose (rhamnose/flavonoid) is from 0.8 to 1.2, wherein the flavonoid inclusion compound comprises isoquercitrin included by γ-cyclodextrin, wherein a molar ratio of the isoquercitrin and the γ-cyclodextrin (γ-cyclodextrin/isoquercitrin) is from 0.9 to 1.8, and wherein a solubility of the isoquercitrin in water is 2% or more.

2. A flavonoid inclusion compound-containing composition comprising a flavonoid inclusion compound and a rhamnose, wherein a molar ratio of a flavonoid in the flavonoid inclusion compound and the rhamnose (rhamnose/flavonoid) is from 0.8 to 1.2, wherein the flavonoid inclusion compound comprises isoquercitrin included by γ-cyclodextrin, wherein a molar ratio of the isoquercitrin and the γ-cyclodextrin (γ-cyclodextrin/isoquercitrin) is from 0.9 to 4.0, and wherein a solubility of the isoquercitrin in water is 2.5% or more.

3. The flavonoid inclusion compound according to claim 1 or claim 2, wherein a molar ratio of the isoquercitrin and the γ-cyclodextrin (γ-cyclodextrin/isoquercitrin) is from 1.0 to 1.8.

4. A flavonoid inclusion compound-containing composition comprising a flavonoid inclusion compound and a rhamnose, wherein a molar ratio of a flavonoid in the flavonoid inclusion compound and the rhamnose (rhamnose/flavonoid) is from 0.8 to 1.2, wherein the flavonoid inclusion compound comprises isoquercitrin included by β-cyclodextrin, wherein a molar ratio of the isoquercitrin and the β-cyclodextrin (β-cyclodextrin/isoquercitrin) is from 1.0 to 3.0, and wherein a solubility of the isoquercitrin in water is 0.1% or more.

5. A flavonoid inclusion compound-containing composition comprising a flavonoid inclusion compound and a rhamnose, wherein a molar ratio of a flavonoid in the flavonoid inclusion compound and the rhamnose (rhamnose/flavonoid) is from 0.8 to 1.2, wherein the flavonoid inclusion compound comprises hesperetin-7-glucoside included by a cyclodextrin, wherein a molar ratio of the hesperetin-7-glucoside and the cyclodextrin (cyclodextrin/hesperetin-7-glucoside) is from 1.0 to 3.0, and wherein a solubility of the hesperetin-7-glucoside in water is 0.01% or more, wherein the cyclodextrin is one or more members selected from the group consisting of β-cyclodextrin and γ-cyclodextrin.

6. The flavonoid inclusion compound-containing composition according to claim 5, wherein a molar ratio of the hesperetin-7-glucoside and the cyclodextrin (cyclodextrin/hesperetin-7-glucoside) is from 1.0 to 1.9.

7. A flavonoid inclusion compound-containing composition comprising a flavonoid inclusion compound and a rhamnose, wherein a molar ratio of a flavonoid in the flavonoid inclusion compound and the rhamnose (rhamnose/flavonoid) is from 0.8 to 1.2, wherein the flavonoid inclusion compound comprises a naringenin-7-glucoside included by β-cyclodextrin, wherein a molar ratio of the naringenin-7-glucoside and the β-cyclodextrin (β-cyclodextrin/naringenin-7-glucoside) is from 1.0 to 3.0, and wherein a solubility of the naringenin-7-glucoside in water is 0.01% or more.

* * * * *

UNITED STATES PATENT AND TRADEMARK OFFICE
CERTIFICATE OF CORRECTION

PATENT NO. : 10,519,182 B2
APPLICATION NO. : 16/097120
DATED : December 31, 2019
INVENTOR(S) : Masamitsu Moriwaki et al.

Page 1 of 2

It is certified that error appears in the above-identified patent and that said Letters Patent is hereby corrected as shown below:

In the Specification

At Column 4, Line 45, please change formula (2):

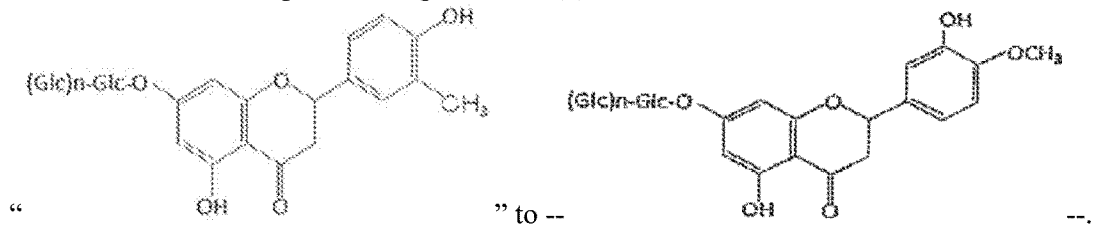

At Column 10, Line 50, please remove formula (2):

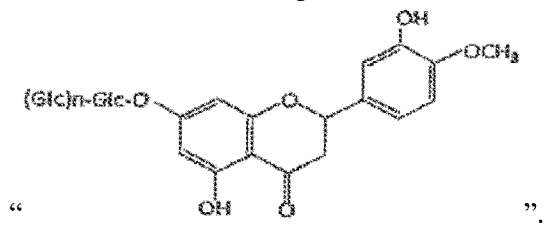

At Column 15, Line 44, please change formula (2):

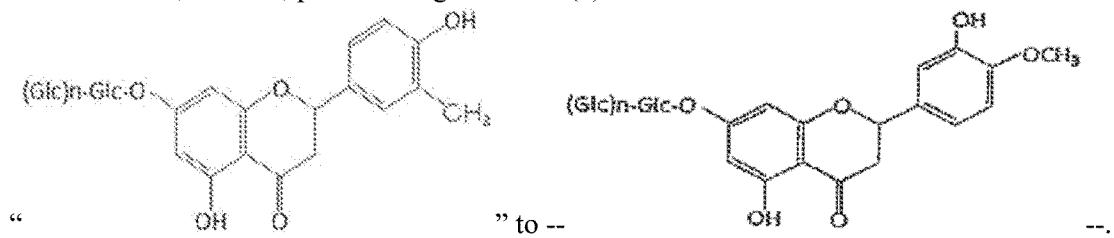

At Column 30, Line 5, please change formula (2):

Signed and Sealed this
Thirtieth Day of June, 2020

Andrei Iancu
*Director of the United States Patent and Trademark Office*

CERTIFICATE OF CORRECTION (continued)
U.S. Pat. No. 10,519,182 B2

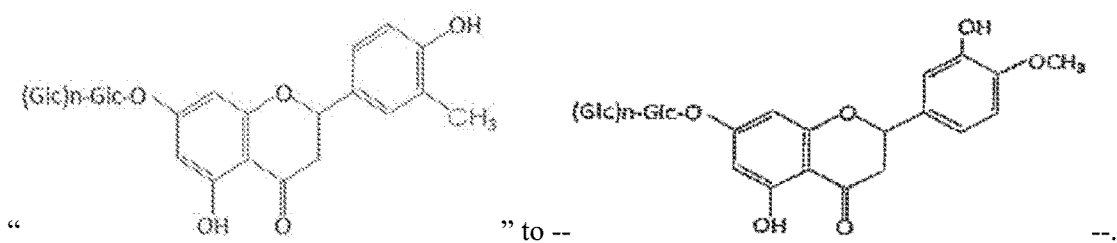

" to --  --.